(12) United States Patent
Ashihara et al.

(10) Patent No.: US 10,898,098 B2
(45) Date of Patent: Jan. 26, 2021

(54) MYOCARDIAL EXCITATION DETERMINING APPARATUS

(71) Applicants: SHIGA UNIVERSITY OF MEDICAL SCIENCE, Otsu (JP); NIHON KOHDEN CORPORATION, Tokyo (JP); Takeshi Tsuchiya, Kumamoto (JP); NATIONAL CEREBRAL AND CARDIOVASCULAR CENTER, Suita (JP)

(72) Inventors: Takashi Ashihara, Otsu (JP); Koji Takizawa, Tokyo (JP); Tatsuo Nishihara, Tokyo (JP); Nobuhiro Suzuki, Tokyo (JP); Yuuho Iwanaga, Tokyo (JP); Akio Ota, Tokyo (JP); Takeshi Tsuchiya, Kumamoto (JP); Kazuo Nakazawa, Suita (JP); Shin Inada, Suita (JP)

(73) Assignees: SHIGA UNIVERSITY OF MEDICAL SCIENCE, Shiga (JP); NIHON KOHDEN CORPORATION, Tokyo (JP); Takeshi TSUCHIYA, Kumamoto (JP); NATIONAL CEREBRAL AND CARDIOVASCULAR CENTER, Osaka (JP)

( * ) Notice: Subject to any disclaimer, the term of this patent is extended or adjusted under 35 U.S.C. 154(b) by 211 days.

(21) Appl. No.: 16/085,095

(22) PCT Filed: Mar. 14, 2017

(86) PCT No.: PCT/JP2017/010287
§ 371 (c)(1),
(2) Date: Sep. 14, 2018

(87) PCT Pub. No.: WO2017/159705
PCT Pub. Date: Sep. 21, 2017

(65) Prior Publication Data
US 2019/0076041 A1    Mar. 14, 2019

(30) Foreign Application Priority Data

Mar. 15, 2016 (JP) ................................ 2016-050782

(51) Int. Cl.
*A61B 5/046* (2006.01)
*A61B 5/00* (2006.01)
(Continued)

(52) U.S. Cl.
CPC ............ *A61B 5/046* (2013.01); *A61B 5/7264* (2013.01); *A61B 5/743* (2013.01); *G16H 50/20* (2018.01);
(Continued)

(58) Field of Classification Search
None
See application file for complete search history.

(56) References Cited

U.S. PATENT DOCUMENTS

| 5,876,349 A | 3/1999 | Wang et al. |
| 2010/0094274 A1 | 4/2010 | Narayan et al. |

(Continued)

FOREIGN PATENT DOCUMENTS

| JP | 2011-143060 A | 7/2011 |
| JP | 2013-523344 A | 6/2013 |

(Continued)

OTHER PUBLICATIONS

Written Opinion (PCT/ISA/237) issued by the International Searching Authority in corresponding International Application No. PCT/JP2017/010287, dated May 23, 2017.
(Continued)

*Primary Examiner* — Kennedy Schaetzle
(74) *Attorney, Agent, or Firm* — Sughrue Mion, PLLC

(57) ABSTRACT

A myocardial excitation determining apparatus which can support the determination of excitation dynamics of the
(Continued)

myocardium during atrial fibrillation is provided. A myocardial excitation determining apparatus has: an acquiring section 2 which acquires an intracardiac electrocardiogram of a subject; a processing section 3 which computes to produce visualized data indicating a state of excitation in the myocardium, based on the intracardiac electrocardiogram; and a determining section 4 which determines the type of excitation dynamics of the myocardium based on the visualized data.

5 Claims, 22 Drawing Sheets

(51) Int. Cl.
*G16H 50/20* (2018.01)
*A61B 5/042* (2006.01)

(52) U.S. Cl.
CPC ........... *A61B 5/0422* (2013.01); *A61B 5/6857* (2013.01); *A61B 2505/05* (2013.01)

(56) References Cited

U.S. PATENT DOCUMENTS

| | | |
|---|---|---|
| 2011/0251505 A1 | 10/2011 | Narayan et al. |
| 2013/0006131 A1 | 1/2013 | Narayan et al. |
| 2013/0150740 A1 | 6/2013 | Narayan et al. |
| 2013/0150742 A1 | 6/2013 | Briggs et al. |
| 2013/0245476 A1 | 9/2013 | Takizawa et al. |
| 2013/0331718 A1 | 12/2013 | Narayan et al. |
| 2014/0052013 A1 | 2/2014 | Narayan et al. |
| 2014/0052127 A1 | 2/2014 | Narayan et al. |
| 2014/0088395 A1 | 3/2014 | Dubois et al. |
| 2014/0114204 A1 | 4/2014 | Narayan et al. |
| 2014/0200429 A1 | 7/2014 | Spector et al. |
| 2014/0200430 A1 | 7/2014 | Spector |
| 2014/0200471 A1 | 7/2014 | Spector |
| 2014/0200571 A1 | 7/2014 | Spector |
| 2014/0200572 A1 | 7/2014 | Spector |
| 2014/0200575 A1 | 7/2014 | Spector |
| 2014/0213922 A1 | 7/2014 | Narayan et al. |
| 2014/0228696 A1 | 8/2014 | Narayan et al. |
| 2014/0276152 A1 | 9/2014 | Narayan et al. |
| 2014/0371609 A1 | 12/2014 | Narayan et al. |
| 2014/0371613 A1 | 12/2014 | Narayan et al. |
| 2014/0371616 A1 | 12/2014 | Narayan et al. |
| 2015/0038861 A1 | 2/2015 | Narayan et al. |
| 2015/0119672 A1 | 4/2015 | Thakur et al. |
| 2015/0254893 A1 | 9/2015 | Laughner et al. |
| 2015/0289807 A1 | 10/2015 | Narayan et al. |
| 2016/0015283 A1 | 1/2016 | Narayan et al. |
| 2016/0022163 A1 | 1/2016 | Narayan et al. |
| 2016/0095531 A1 | 4/2016 | Narayan et al. |
| 2016/0166167 A1 | 6/2016 | Narayan et al. |
| 2016/0235311 A1 | 8/2016 | Narayan et al. |
| 2016/0278657 A1 | 9/2016 | Narayan et al. |
| 2016/0324434 A1 | 11/2016 | Briggs et al. |
| 2016/0338772 A1 | 11/2016 | Dubois et al. |
| 2016/0374571 A1 | 12/2016 | Narayan et al. |
| 2017/0079542 A1 | 3/2017 | Spector |
| 2017/0156616 A1* | 6/2017 | Talkachova ............ A61B 5/046 |
| 2017/0232263 A1 | 8/2017 | Narayan et al. |
| 2017/0245774 A1 | 8/2017 | Narayan et al. |
| 2017/0311835 A1 | 11/2017 | Narayan et al. |
| 2017/0332971 A1* | 11/2017 | Macneil ............ A61B 5/02405 |
| 2017/0367603 A1 | 12/2017 | Spector |

FOREIGN PATENT DOCUMENTS

| | | |
|---|---|---|
| JP | 2013-188439 A | 9/2013 |
| JP | 2015-530160 A | 10/2015 |
| JP | 2016-504117 A | 2/2016 |
| WO | 2010054409 A1 | 5/2010 |
| WO | 2015066678 A2 | 5/2015 |

OTHER PUBLICATIONS

International Search Report (PCT/ISA/210), issued by International Searching Authority in corresponding International Application No. PCT/JP2017/010287, dated May 23, 2017.

Communication dated Feb. 4, 2020, from the Japanese Patent Office in counterpart application No. 2016-050782.

* cited by examiner

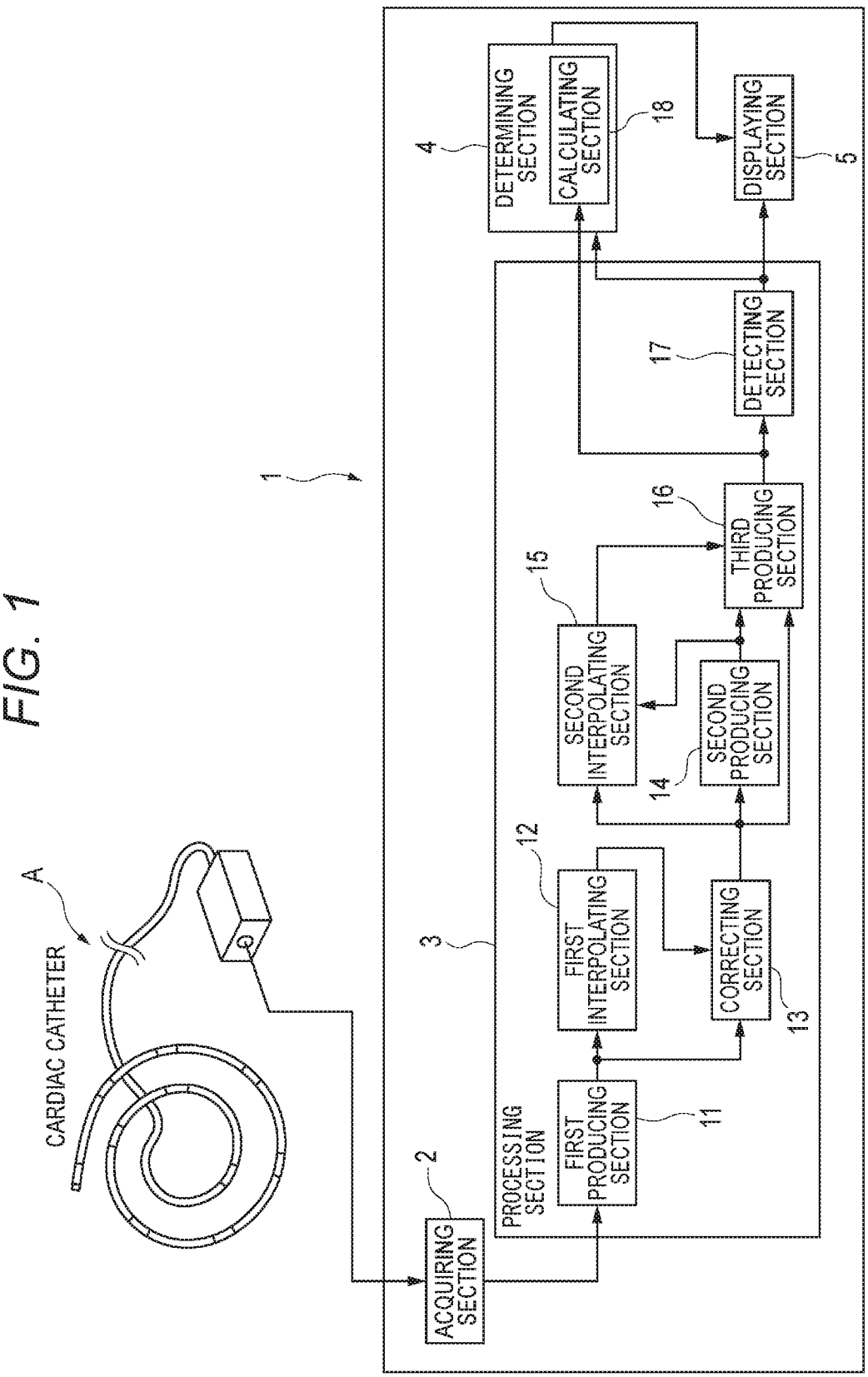

Meandering Rotor

Passive Activation

Multiple Wavelets

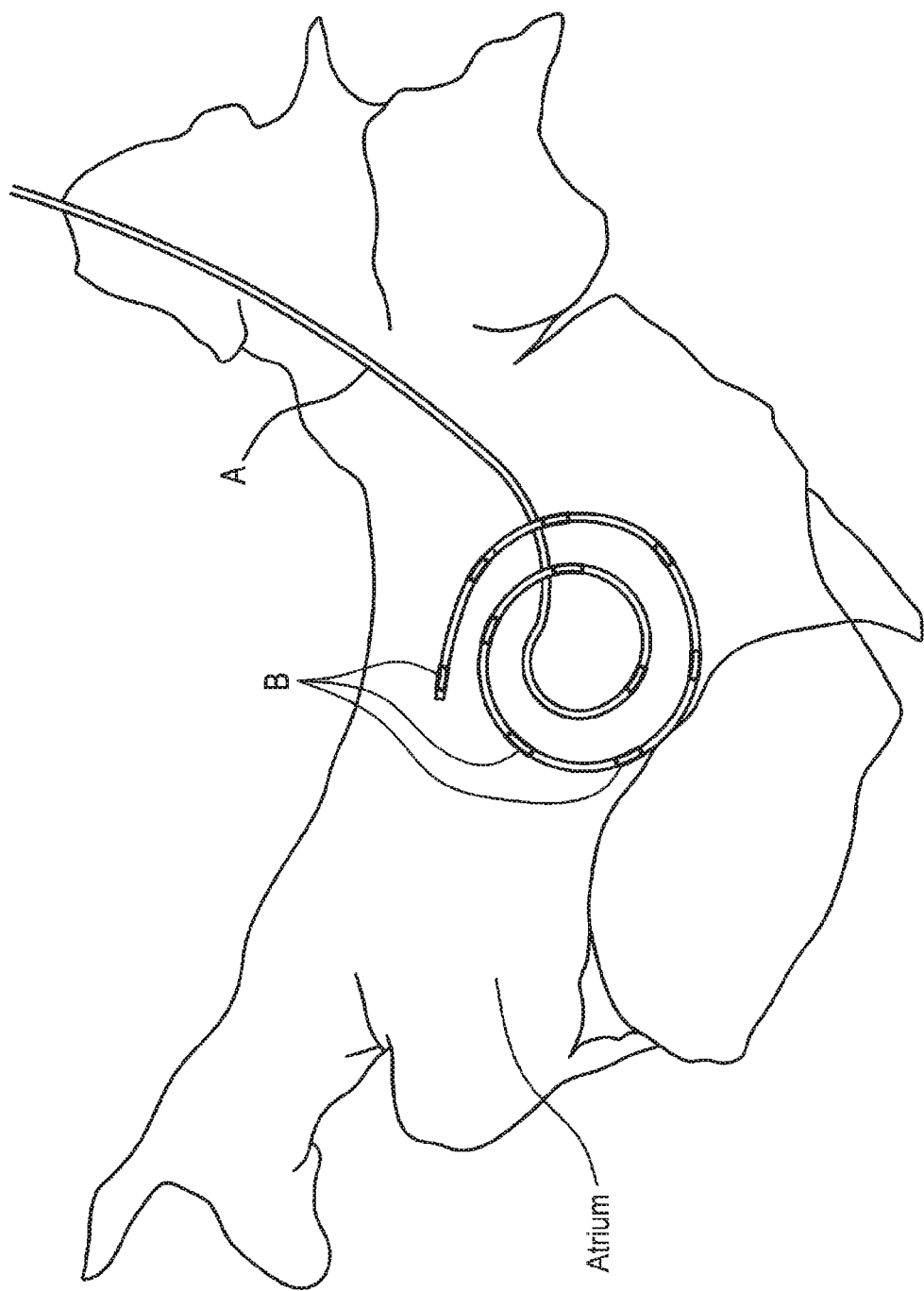

First Sample    Second Sample    X-th Sample

FIG. 25
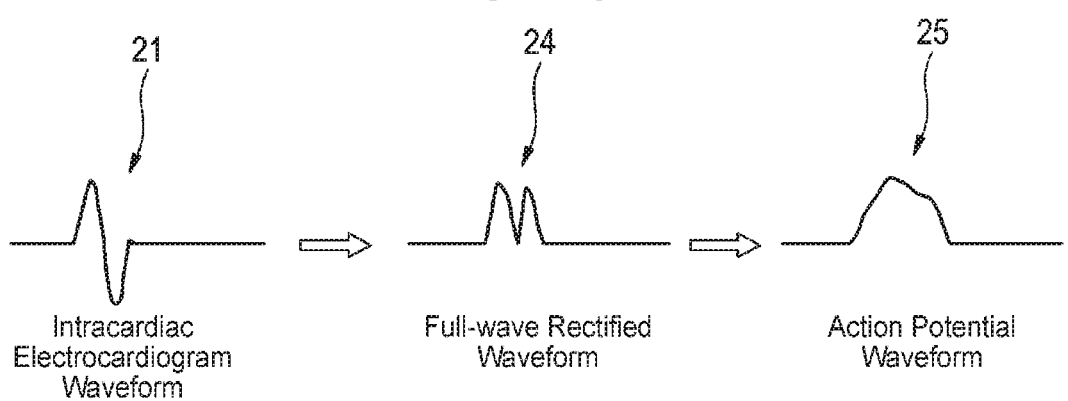
Intracardiac Electrocardiogram Waveform
Full-wave Rectified Waveform
Action Potential Waveform
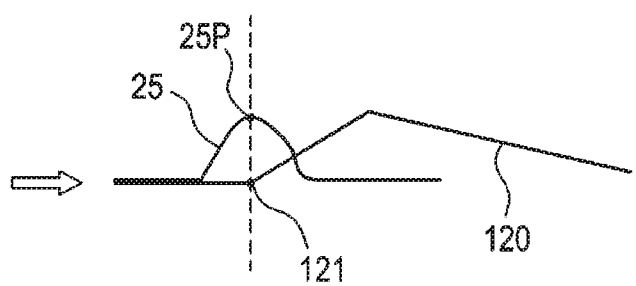

MYOCARDIAL EXCITATION DETERMINING APPARATUS

TECHNICAL FIELD

The present invention relates to a myocardial excitation determining apparatus for determining the type of excitation in the myocardium.

BACKGROUND ART

Usually, atrial fibrillation means an arrhythmia in which the atrium of the heart has a convulsive seizure, and the heart cannot operate in the original and correct way. When atrial fibrillation occurs, the blood stagnates in the atrium, and thrombus is prone to develop, thereby increasing the possibility of occurrence of brain infarction or the like.

Conventionally, it is known that, when an arrhythmia such as atrial fibrillation occurs, a treatment is performed by selectively applying ablation to an abnormal portion which causes the arrhythmia, by using a cardiac catheter. In the treatment, it is important to correctly identify the location where ablation is to be performed. For example, JP2013-523344T and U.S. Patent Publication No. 2014/0088395 disclose a technique in which a calculation process is performed on an intracardiac electrocardiogram that is measured from electrodes of a cardiac catheter, thereby producing visualized data indicating the state of excitation in the myocardium, and the location where ablation is to be performed is identified from the visualized data.

States of myocardial excitation during atrial fibrillation are roughly classified into several types such as those called typical excitation dynamics, according to the change pattern of the state.

In the related art, the medical person must determine the type of excitation dynamics of the myocardium by means of visual observation of the state of the myocardium. However, the state of the myocardium during atrial fibrillation has characteristics that it irregularly varies from time to time. In some cases, the variation is so rapid that it cannot be visually recognized, and it is difficult to visually determine the type.

Therefore, it is an object of the invention to provide a myocardial excitation determining apparatus which can support the determination of excitation dynamics of the myocardium during atrial fibrillation.

SUMMARY

An aspect of the myocardial excitation determining apparatus of the invention includes:
  an acquiring section which acquires an intracardiac electrocardiogram of a subject;
  a processing section which computes to produce visualized data indicating a state of excitation in a myocardium, based on the intracardiac electrocardiogram; and
  a determining section which determines a type of excitation dynamics of the myocardium based on the visualized data.

According to the configuration, the type of excitation dynamics of the myocardium during atrial fibrillation is automatically determined based on the visualized data. Therefore, the medical person can determine the type of excitation dynamics of the myocardium by reference to the result of the automatic determination.

As described above, the above-described configuration can provide a myocardial excitation determining apparatus which can support the determination of excitation dynamics of the myocardium during atrial fibrillation.

BRIEF DESCRIPTION OF DRAWINGS

FIG. 1 is a diagram of a myocardial excitation determining apparatus of Embodiment 1 of the invention.

FIG. 3 is a diagram illustrating a catheter in the atrium.

FIG. 25 illustrates a display position of an action potential unit waveform with respect to an intracardiac electrocardiogram waveform.

DESCRIPTION OF EMBODIMENTS

Figure 2A:
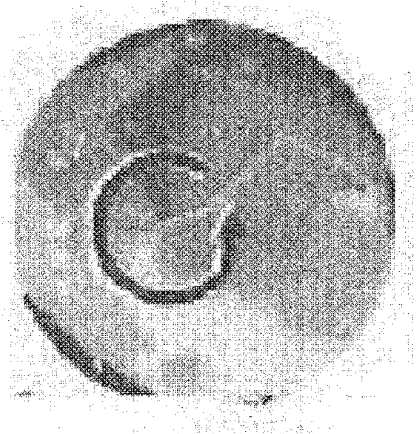
FIG. 2A to 2C illustrates a typical types of excitation dynamics of the myocardium.

Hereinafter, embodiments will be described with reference to the drawings.

Embodiment 1

As shown in FIG. 1, a myocardial excitation determining apparatus 1 of Embodiment 1 includes an acquiring section 2, a processing section 3, a determining section 4, and a displaying section 5. For example, the myocardial excitation determining apparatus 1 is used for performing one function of a catheter inspecting apparatus.

The acquiring section 2 acquires an intracardiac electrocardiogram of a subject which is acquired or recorded by a recording unit (e.g., a cardiac catheter, spiral catheter, helix catheter) A having a plurality of electrodes.

The processing section 3 performs a computation for visualizing the state of myocardial excitation of the subject, on the intracardiac electrocardiogram which is acquired by the acquiring section 2. The processing section 3 includes a first producing section 11, a first interpolating section 12, a correcting section 13, a second producing section 14, a second interpolating section 15, a third producing section 16, and a detecting section 17.

The first producing section 11 produces pseudo action potential waveforms with respect to a plurality of intracardiac electrocardiograms which are acquired by the acquiring section 2, respectively. The first interpolating section 12 defines a virtual electrode at a position which is in the myocardium of the atrium, and in which no electrode of the inserted cardiac catheter A is placed, i.e., at a position in which the distances with respect to surrounding electrodes among the placed electrodes are large. The first interpolating section 12 interpolates a pseudo action potential waveform with respect to the virtual electrode, based on pseudo action potential waveforms which are produced with respect to electrodes surrounding the virtual electrode.

The correcting section 13 reduces noise components contained in the pseudo action potential waveforms output from the first producing section 11 and the first interpolating section 12, and performs a correction in which the amplitudes at respective beats are made uniform. In the following description of Embodiment 1, a corrected action potential waveform is referred to simply as an action potential waveform. With respect to each of the action potential waveforms output from the correcting section 13, the second producing section 14 produces a shifted waveform which is shifted in time phase by a predetermined time from the action potential waveform. With respect to a position in which the electrodes of the cardiac catheter A and the virtual electrode are not placed, i.e., the distances between each electrode and surrounding electrodes are large, the second interpolating section 15 interpolates an action potential waveform and a shifted waveform based on the action potential waveforms and shifted waveforms which are produced with respect to the surrounding electrodes.

The third producing section 16 produces a phase portrait based on the action potential waveforms output from the correcting section 13, the shifted waveforms output from the second producing section 14, and the action potential waveforms and shifted waveforms output from the second interpolating section 15. Moreover, the third producing section 16 calculates the phase based on the phase portrait, and produces visualized data (Phase Map) indicating the state of excitation in the myocardium. The visualized data mean a frame in which the excitation potential of the myocardium is visualized. Electrical excitation occurs in the membrane potential of the myocardium cells to cause the heart to contract. The excitation-contraction phenomenon is provoked by the action potential. The action potential is an excitation reaction of myocardial cells which is caused by depolarization produced by the flow of $Na^+$ into the cells, and repolarization produced by the flow in or out of $Ca^{2+}$ or $K^+$.

The detecting section 17 detects a phase singularity in the visualized data produced by the third producing section 16, i.e., the rotor of fibrillation on the atrial wall.

The determining section 4 determines the type of excitation dynamics of the myocardium based on visualized data. The determining section 4 has a calculating section 18 for calculating the number of predetermined data contained in the visualized data. The visualized data for determining the type of excitation dynamics of the myocardium are configured by frames of predetermined time units. The calculating section 18 calculates the total number of predetermined grids included in the frames of predetermined time units, as the number of predetermined data contained in the visualized data. The determining section 4 determines the type of excitation dynamics of the myocardium, based on the number of predetermined grids which is calculated by the calculating section 18, and the number of phase singularities detected by the detecting section 17.

The displaying section 5 displays the state of excitation in the myocardium of the subject, and the determined type of excitation dynamics, based on the visualized data output from the third producing section 16 of the processing section 3. The displaying section 5 is configured by, for example, a liquid crystal monitor screen of the touch panel type.

Figure 2B:
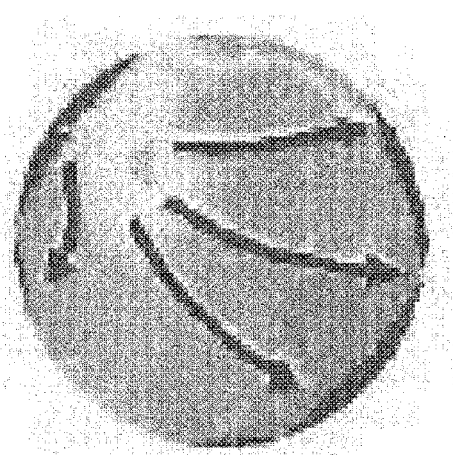
Figure 2C:
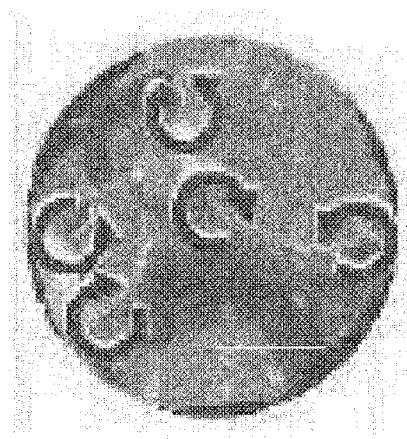

The type of excitation dynamics of the myocardium means a change pattern of the myocardium condition in which atrial fibrillation occurs. The type of excitation dynamics of the myocardium includes the MR (Meandering Rotor) as shown in FIG. 2A, the PA (Passive Activation) as shown in FIG. 2B, and the MW (Multiple Wavelets) as shown in FIG. 2C. The MR is a state where the excitation wave rotates around a phase singularity. The PA is a state where the excitation wave propagates. The MW is a state where a plurality of phase singularities exist simultaneously.

Next, the operation of the myocardial excitation determining apparatus 1 will be described with reference to FIGS. 3 to 19.

As shown in FIG. 3, first, the cardiac catheter A having a plurality of electrodes B is inserted and placed in the atrium of the subject.

As shown in FIG. 4A, a plurality (in the embodiment, ten waveforms) of intracardiac electrocardiogram waveforms 21a to 21j (hereinafter, "intracardiac electrocardiogram waveforms 21" is used when generally referring to the intracardiac electrocardiogram waveforms) are recorded by the electrodes B of the cardiac catheter A. The recorded intracardiac electrocardiogram waveforms 21 are acquired by the acquiring section 2.

Figure 4:
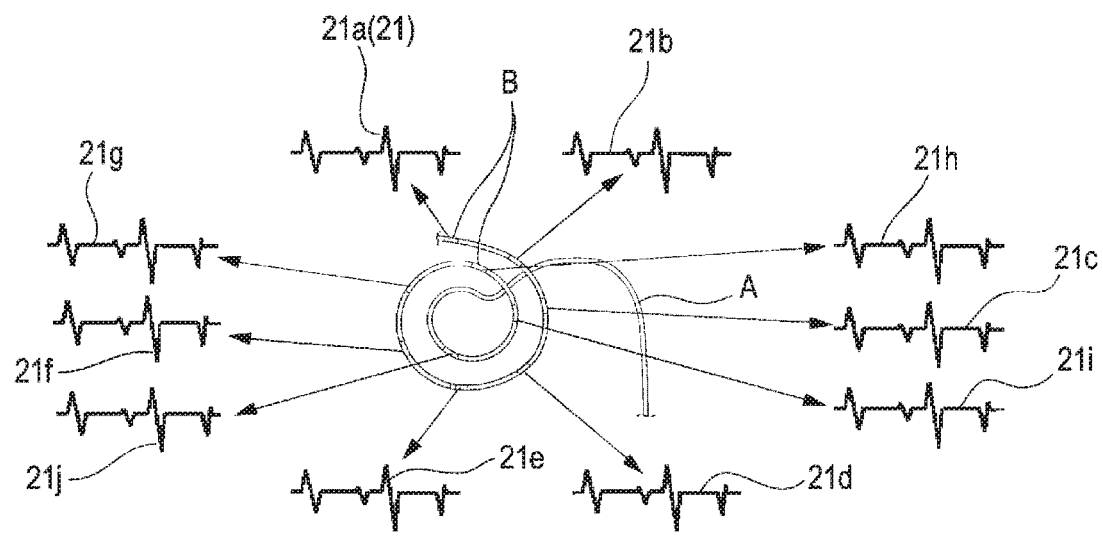
FIG. 4A is a diagram illustrating examples of intracardiac electrocardiogram waveforms which are acquired by electrodes.
FIG. 4B is a diagram of a placement of the acquired intracardiac electrocardiograms on grids.
Figure 4B:
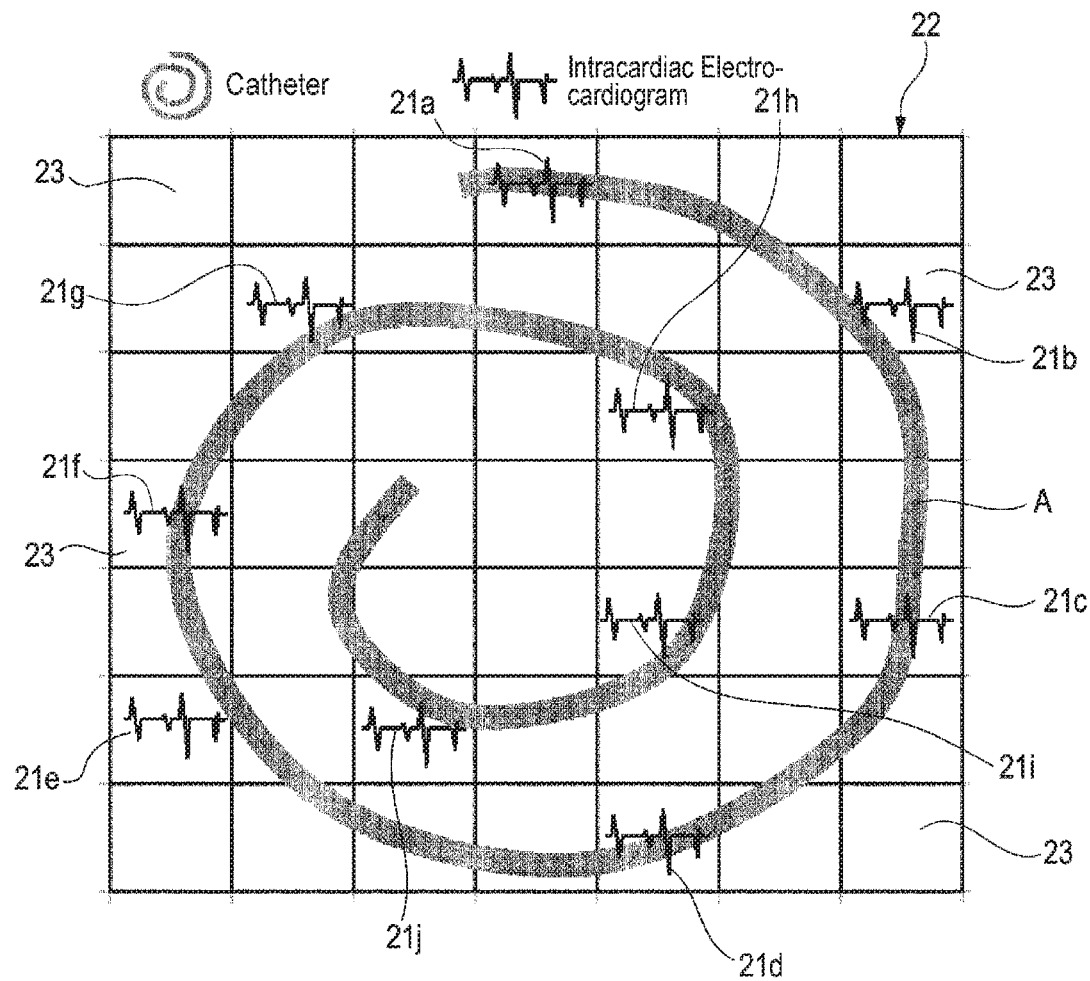

As shown in FIG. 4B, the first producing section 11 shows a predetermined region in the atrium in which the cardiac catheter A is placed as a rectangular frame 22 or the like, and partitions the frame 22 into a plurality of grids 23. In the diagram of FIG. 4B, for the sake of convenience of description, 7×7=49 grids are shown. Actually, however, the frame is partitioned into several tens of thousands or more of grids. In accordance with the position of the cardiac catheter A placed in the atrium, the positions of the electrodes B are shown on the corresponding grids in the frame, and the intracardiac electrocardiogram waveforms 21a to 21j are placed on the grids 23, respectively.

Figure 5A:
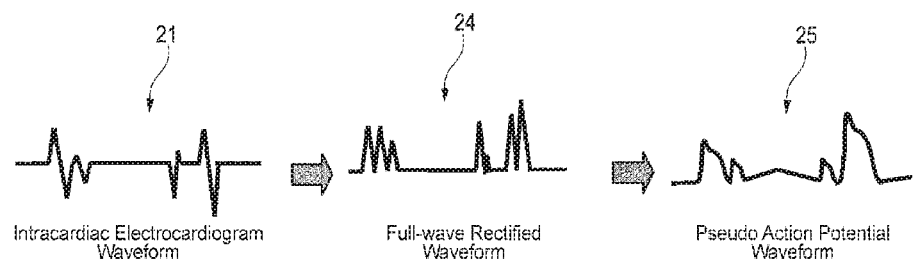
FIG. 5A illustrates steps of producing a pseudo action potential waveform.
Figure 5:
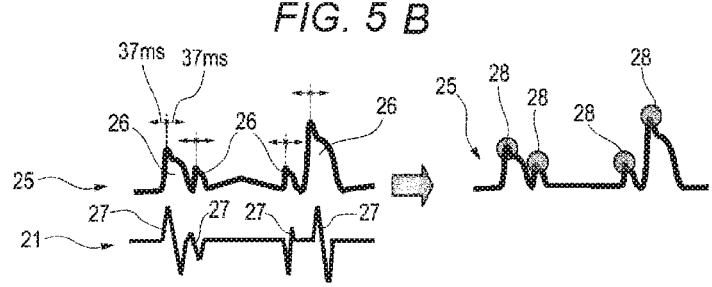
FIG. 5B is a view illustrating steps of detecting beats.
Figure 6:
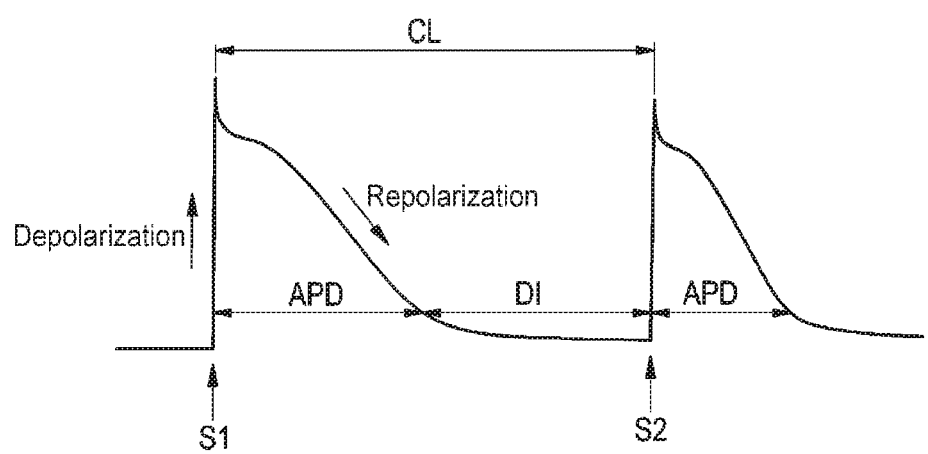
FIG. 6A illustrates a diastolic interval and an action potential duration.
FIG. 6B is a graph showing relationships between a diastolic interval and an action potential duration.
FIG. 6C is a view showing conditions for detecting beats.
Figure 6:
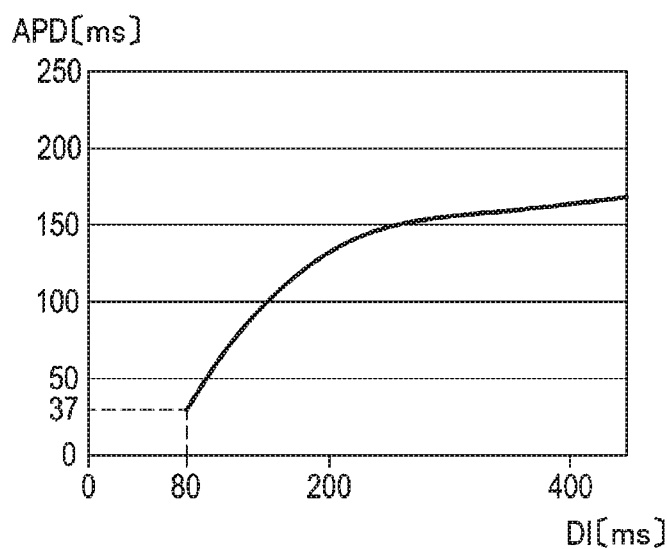
Figure 6:
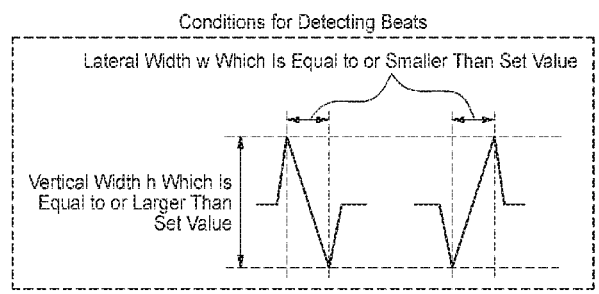

As shown in FIG. 5A, the first producing section 11 full-wave rectifies each of the intracardiac electrocardiogram waveforms 21 to produce a full-wave rectified waveform 24. Moreover, the first producing section 11 performs moving average of the full-wave rectified waveform 24 to produce a pseudo action potential waveform 25.

As shown in FIG. 5B, furthermore, the first producing section 11 detects candidates of beats (beat candidates) 28 indicating the diastoles of the myocardium in the pseudo action potential waveform 25, based on the pseudo action potential waveform 25 and the intracardiac electrocardiogram waveform 21. Specifically, the first producing section 11 first detects, in the pseudo action potential waveform 25, convex portions 26 with respect to each of which a larger portion does not exist within time periods of 37 msec. (described later with reference to FIGS. 6A and 6B) preceding and succeeding the convex portion 26. Then, the first producing section 11 detects, in the intracardiac electrocardiogram waveform 21, beats 27 which are in phase with the respective convex portions 26, and which satisfy predetermined conditions (described later with reference to FIG. 6C). In the case where a convex portion 26 contains a beat 27 satisfying the predetermined conditions, the first producing section 11 detects the convex portion 26 as a beat candidate 28 indicating the diastole of the myocardium. In FIG. 5B, four beat candidates 28 are detected.

FIG. 6A illustrates an ideal model of a unit waveform contained in the action potential waveform of the myocardium. In FIG. 6A, the term "APD" (Action Potential Duration) means a time period from the start of the depolarization phase of the action potential of the myocardium, to the end of the repolarization phase, and corresponds to the refractory period of the myocardium. The term "DI" (Diastolic Interval) means a time period from the end of the APD to the start of the next APD, and corresponds to the stationary phase when the myocardium is excitable. The total time period of the APD and the DI is called the CL (Cycle Length). The relationships between the DI and the APD in the ideal model of a unit waveform are previously obtained from a computer simulation as shown in the graph of FIG. 6B. As shown in the graph, the periods of 37 msec. are determined with reference to the shortest APD. The predetermined conditions of the beat 27 are set that, as shown in FIG. 6C, the lateral width w of the beat 27 is equal to or smaller than a preset value, and the vertical width h is equal to or larger than a preset value.

As shown in FIG. 7A, then, the first producing section 11 compares the heights of the peaks of all beat candidates (in the embodiment, beat candidates 28a, 28b) which exist in the shortest CL starting from the initial beat candidate 28a, with one another. The first producing section 1 detects the beat candidate 28a having the highest peak as the first beat 29A. From the graph of FIG. 6B, the shortest CL is 117 msec. which is obtained by adding 37 msec. that is the shortest APD, and 80 msec. that is the shortest DI.

Figure 7:
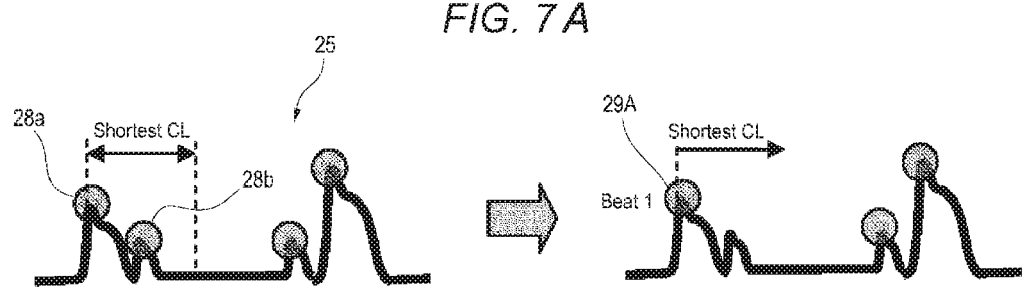
FIG. 7A illustrates steps of detecting the initial beat.
FIG. 7B is a view illustrating steps of detecting the second and subsequent beats.
Figure 7B:
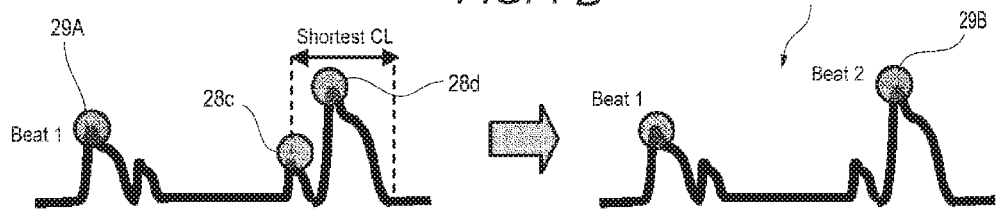

As shown in FIG. 7B, then, the first producing section 11 compares the heights of the peaks of all beat candidates (in the embodiment, beat candidates 28c, 28d) which exist in the shortest CL starting from the beat candidate 28c following the beat candidates 28a, 28b that are compared with each other in FIG. 7A, with one another. The first producing section 11 detects the beat candidate 28d having the highest peak as the second beat 29B. Same or similarly, the first producing section 11 detects beats from pseudo action potential waveforms 25a to 25j which are produced based on the intracardiac electrocardiogram waveforms 21a to 21j, respectively.

Figure 8:
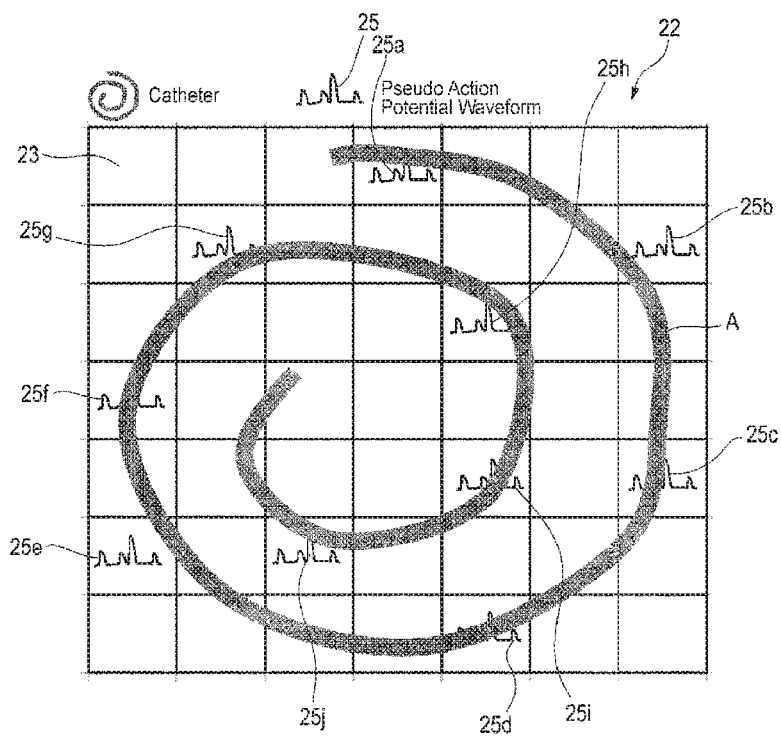
FIG. 8 is a diagram of a placement of pseudo action potential waveforms on grids.

The pseudo action potential waveforms 25a to 25j from which the beats 29A, 29B, . . . are detected are placed on the grids 23 (see FIG. 8).

Figure 9A:
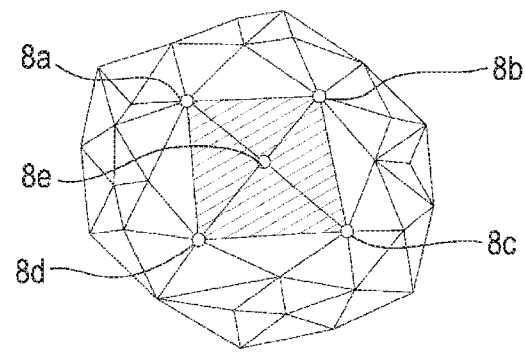
FIG. 9A is a view for calculating virtual electrodes.
Figure 9B:
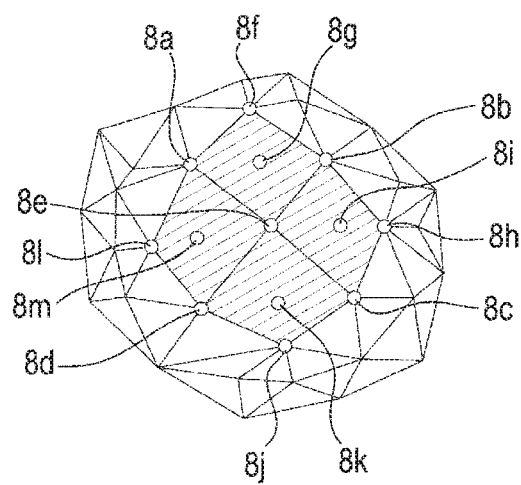
FIG. 9B is a view for calculating virtual electrodes.
Figure 9C:
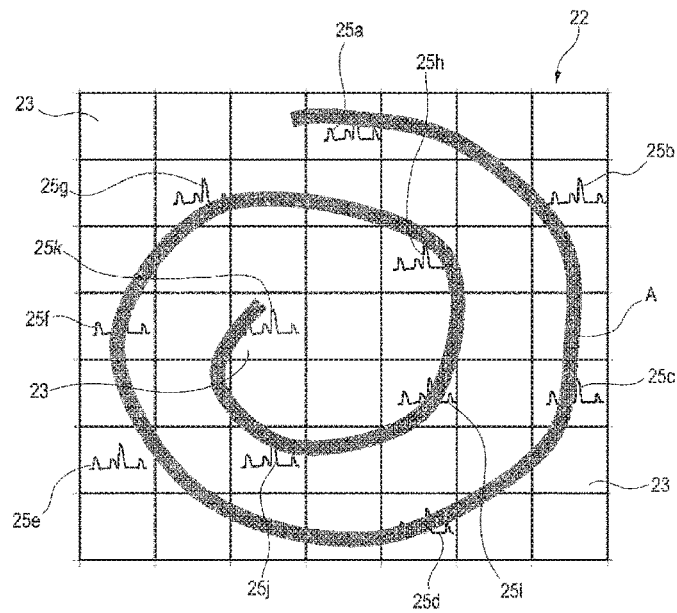
FIG. 9C is a view for calculating virtual electrodes and a diagram of a placement of an action potential waveform of a virtual electrode which is interpolated from surrounding electrodes.

Then, the first interpolating section 12 defines virtual electrodes in locations where the pseudo action potential waveforms 25 are not placed, based on the positions of the pseudo action potential waveforms 25a to 25j which are placed in the frame 22, and which are shown in FIG. 8. As shown in FIGS. 9A and 9B, each of the virtual electrodes is defined based on a plurality (in the embodiment, four) of surrounding electrodes. In FIG. 9A, the position of a virtual electrode 8e is set based on position data of electrodes 8a to 8d. In FIG. 9B, the position of another virtual electrode 8g is set based on the virtual electrode 8e and electrodes 8a, 8b, 8f. The first interpolating section 12 sets the positions of virtual electrodes 8i, 8k, 8m by using a same or similar technique.

The first interpolating section 12 interpolates pseudo action potential waveforms 25 with respect to the defined virtual electrodes 8e, 8g, 8i, 8k, 8m, . . . , based on pseudo action potential waveforms which are produced with respect to surrounding electrodes. For example, an interpolated pseudo action potential waveform 25k is placed on the grid 23 in the location where a virtual electrode is disposed (see FIG. 9C).

Figure 10A:
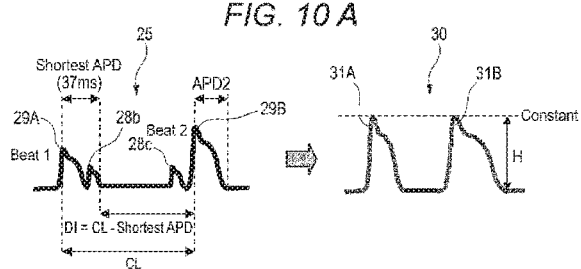
FIG. 10A is a view illustrating steps of correcting the height of a beat.
Figure 10B:
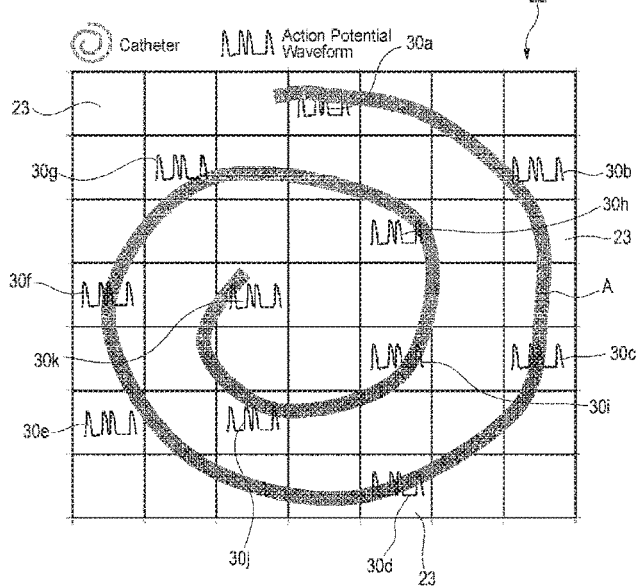
FIG. 10B is a diagram of a placement of action potential waveforms on grids.

As shown in FIG. 10A, then, the correcting section 13 produces action potential waveforms 30 from the pseudo action potential waveform 25. Specifically, the correcting section 13 first applies the shortest APD (37 msec.) to the first beat 29A of the pseudo action potential waveform 25. Then, the CL between the peak of the first beat 29A and that of the second beat 29B is obtained. The shortest APD is subtracted from the CL to obtain the value of the DI (DI=CL−shortest APD). Then, the value of the APD corresponding to the obtained value of the DI is obtained from the graph of FIG. 6B. The obtained value of the APD is the value of the APD2 of the second beat 29B. Same or similarly, the values of the APDs of the third and subsequent beats 29 are obtained.

Then, the correcting section 13 multiplies the beats 29A, 29B, . . . by a correction coefficient, thereby correcting the heights (amplitudes) of the beats to justify the heights. The correction coefficient is obtained by dividing a constant by the height of the beat 29A. 29B, or the like (correction coefficient=constant/height of peak of beat 29). The correcting section 13 eliminates, by correction, beat candidates other than the beats 29A, 29B, etc. in the pseudo action potential waveform 25, such as the beat candidates 28*b*, 28*c*, etc. As a result, the action potential waveforms 30 having beats 31A, 31B, . . . in which their heights H are equal to one another are produced with respect to the pseudo action potential waveforms 25, respectively. The corrected action potential waveforms 30*a* to 30*k* are placed on the grids 23 in the locations where the electrodes and the virtual electrodes are disposed (see FIG. 10B).

Figure 11A:
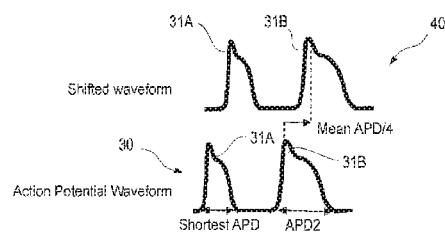
FIG. 11A is a view showing a shifted waveform in which the phase is shifted with respect to an action potential waveform.
Figure 11B:
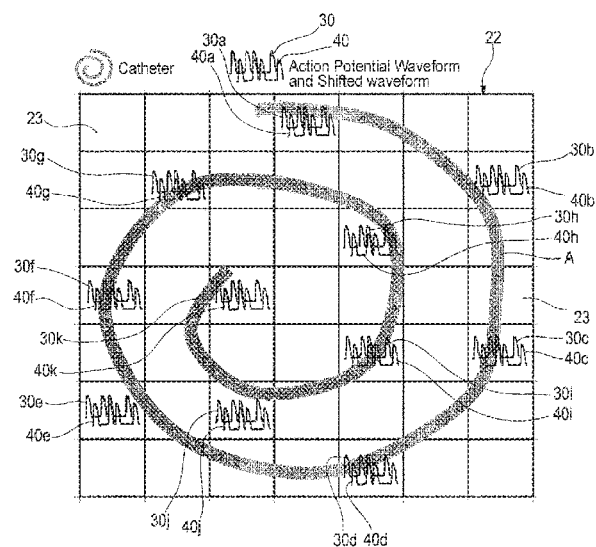
FIG. 11B is a diagram of a placement of action potential waveforms and shifted waveforms on grids.

Then, the second producing section 14 calculates a mean APD of the beats 31A, 31B, . . . in the action potential waveforms 30, and produces shifted waveforms 40 which, as shown in FIG. 11A, are shifted in time phase by ¼ of the mean APD from the action potential waveforms 30. The action potential waveforms 30*a* to 30*k* and the shifted waveforms 40*a* to 40*k* are placed on the grids 23 in the locations where the electrodes and the virtual electrodes are disposed (see FIG. 11B). The magnitude of the shift in time phase may be N+(¼) (N is 0 or a positive integer).

Figure 12A:
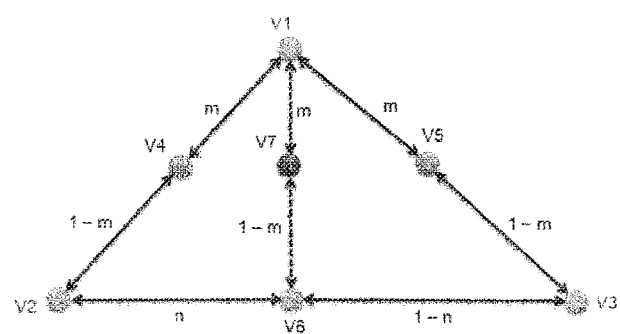
FIG. 12A is a view illustrating a calculation of interpolated waveforms on other grids in which the spatial interpolation technique is used.
Figure 12B:
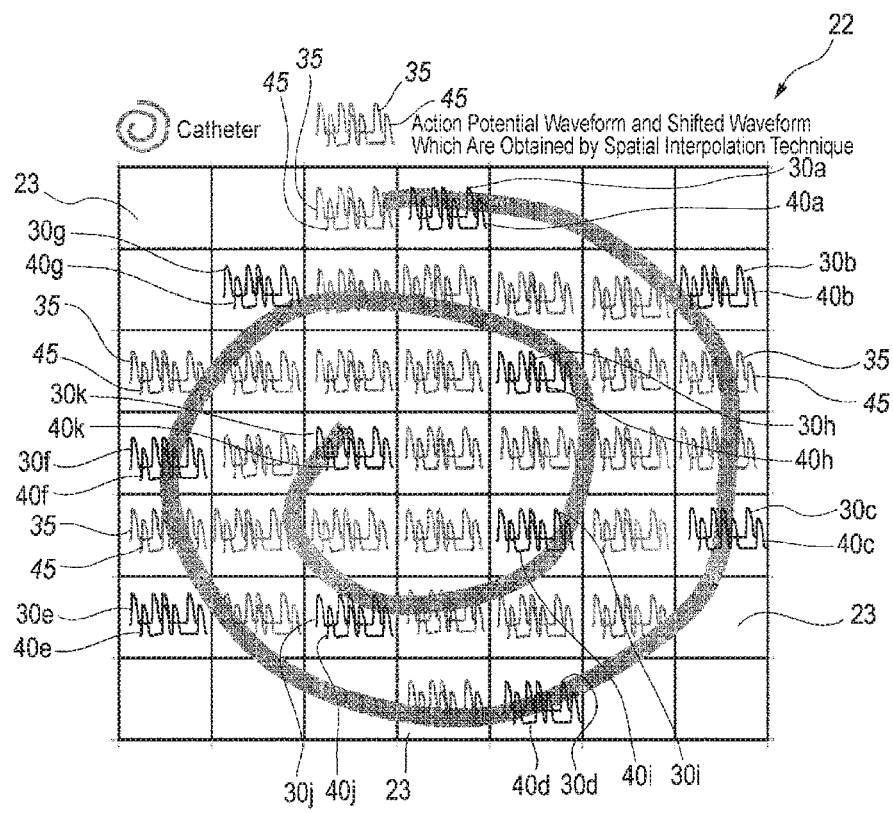
FIG. 12B is a diagram of a placement of interpolated action potential waveforms and shifted waveform on grids.

Then, the second interpolating section 15 interpolates virtual action potential waveforms 35 and virtual shifted waveform 45 to grids 23 (see FIG. 11B) in which the action potential waveforms 30 and the shifted waveforms 40 are not placed on the frame 22. The second interpolating section 15 calculates data of the action potential waveforms 35 and the shifted waveforms 45, from those of the surrounding action potential waveforms 30 and shifted waveforms 40 by using the spatial interpolation technique shown in FIG. 12A. In FIG. 12A, V1 to V3 indicate the data of the action potential waveforms 30 and the shifted waveforms 40 in the grids 23 of the electrodes and the virtual electrodes, and V4 to V7 indicate data of the action potential waveforms 35 and the shifted waveforms 45. The arrows indicate the distances between close grids among grids in which the data V1 to V7 are placed or to be placed. As an example, the distances between the grids are indicated as 1.

From the data of the action potential waveforms 30 and shifted waveforms 40 of two grids which are close to the grid where the action potential waveform 35 and the shifted waveform 45 are to be placed, the data of the action potential waveform 35 and the shifted waveform 45 are calculated according to a predetermined calculation expression, by using the spatial interpolation technique, the data of the two grids, and the distance between the two grids. For example, the action potential waveform 35 and shifted waveform 45 of V4 are calculated from the data of V1 and V2, and the distances m and 1−m between V1 and V4, and V2 and V4. V7 is calculated from V6 which is calculated as described above, and the data V1 of the grid in which the action potential waveforms 30 and the shifted waveforms 40 are placed. The action potential waveforms 35 and shifted waveforms 45 which are calculated as described above are placed on the grids 23 in which the interpolation is performed (see FIG. 12B).

Figure 13:
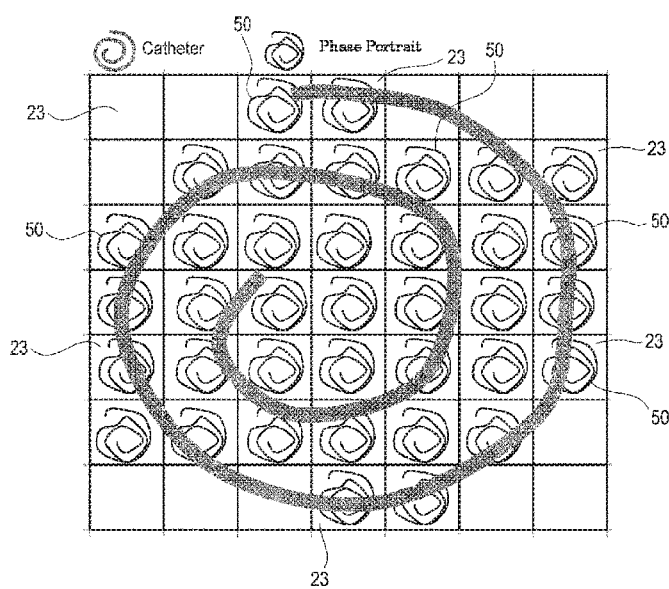
FIG. 13 is a diagram showing a phase portrait drawn in each grid.

In order to obtain the states of the action potentials in the grids 23 in which the action potential waveforms 30, 35 and the shifted waveforms 40, 45 are placed, then, the third producing section 16 produces phase portraits 50 based on the respective action potential waveforms 30, 35 and shifted waveforms 40, 45 as shown in FIG. 13. A phase portrait can be produced by rewriting the potentials of action potential waveforms and shifted waveforms to two-dimensional ones.

Figure 14:
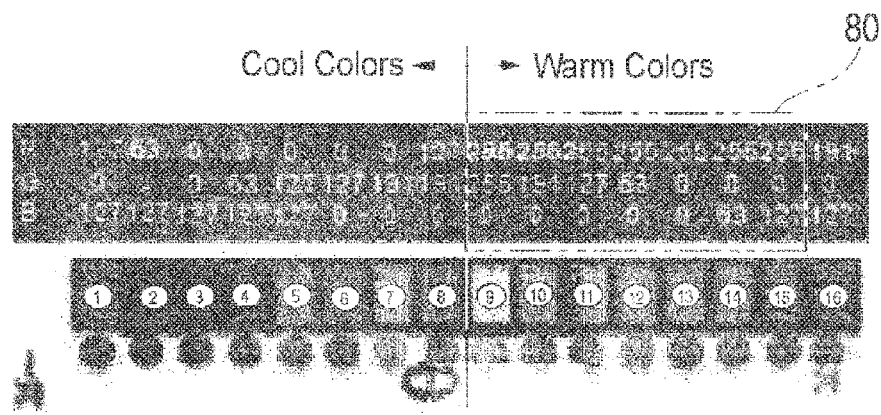
FIG. 14A is a view illustrating colors which are painted in grids, and illustrates colors used in the painting.
FIG. 14B is a view illustrating colors which are painted in grids, a view in which portions of an action potential waveform are defined by colors for every sample.
FIG. 14C is a view illustrating colors which are painted in grids, illustrates angle information of samples.
Figure 14:
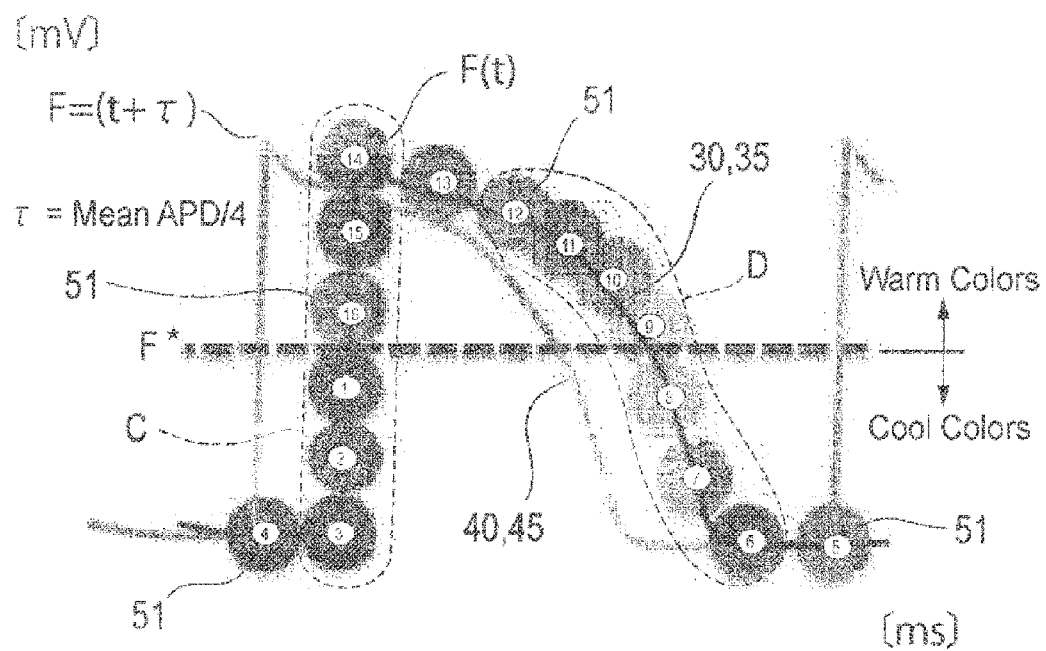
Figure 14C:
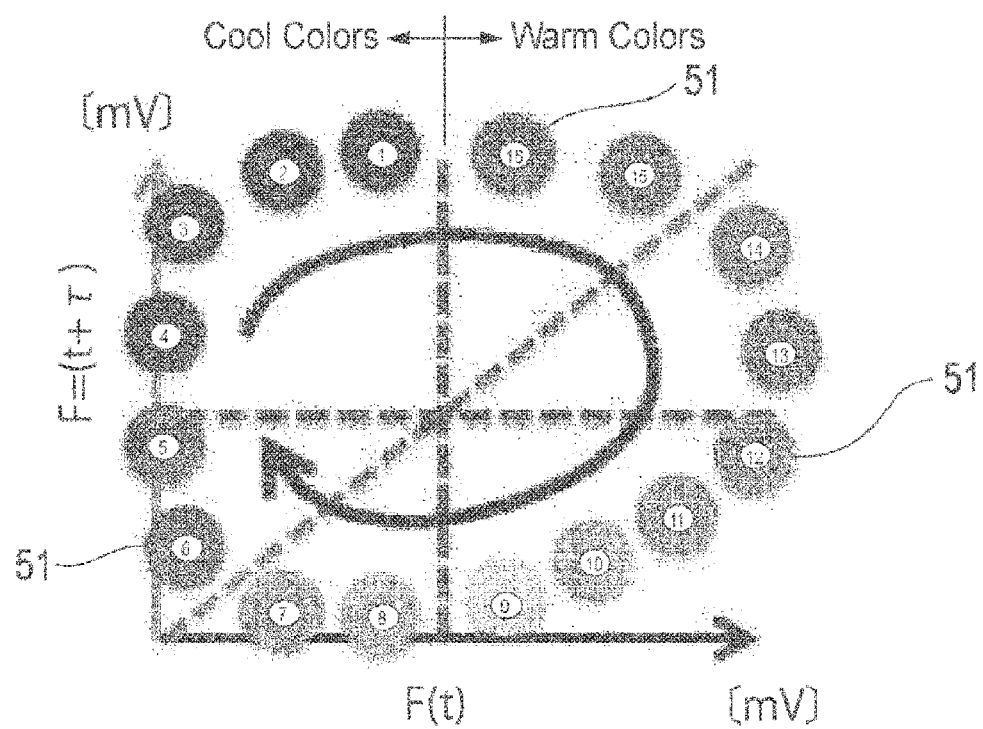

In order to express the states of the action potentials in colors, the third producing section 16 paints the grids 23 with colors. The colors of the grids 23 are determined for respective samples of the produced phase portraits. The third producing section 16 draws the grids 23 by using a plurality of colors (in the embodiment, 16 colors) shown in FIG. 14A. For example, the third producing section 16 defines colors so that, in unit waveforms of the action potential waveforms 30, 35, the action potential portion is drawn in warm colors, and the resting membrane portion is drawn in cool colors (see FIG. 14B). The third producing section 16 further defines colors so that, in the region C where the temporal variation in the action potential is fast, the color change between adjacent samples 51 is small, and, in the region D where the temporal variation is slow, the color change is large. As shown in FIG. 14C, the third producing section 16 obtains angle information of each of the samples 51 from the center portion of a phase portrait which is displayed while being replaced with a two-dimensional form, and expresses the state of the action potential of the sample by one of 16 colors.

Figure 15A:
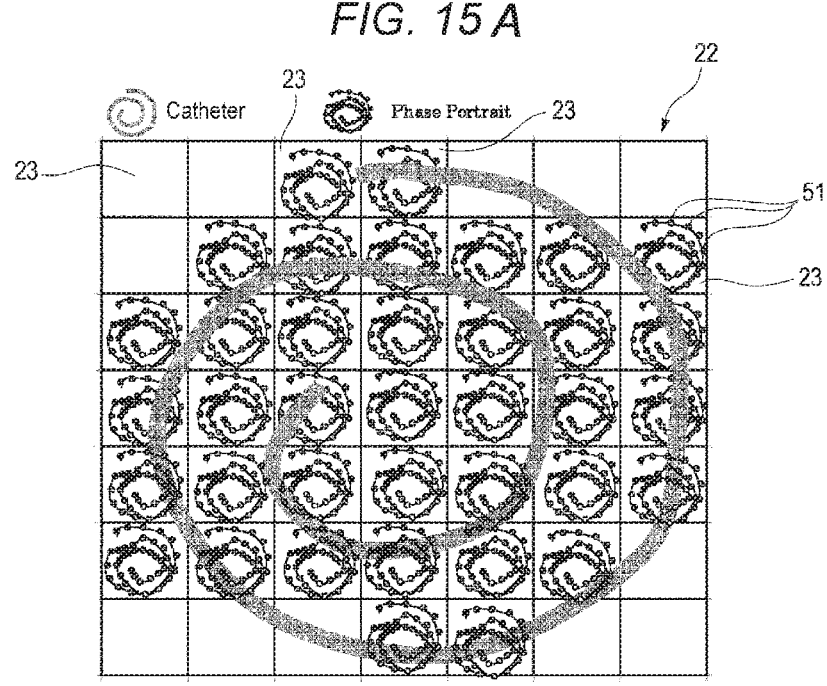
FIG. 15A is a diagram in which each sample is colored in each grid.
Figure 15B:
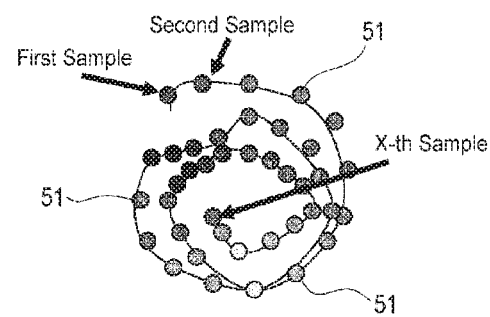
FIG. 15B is a view in which first to X-th samples in one grid are colored.
Figure 15C:
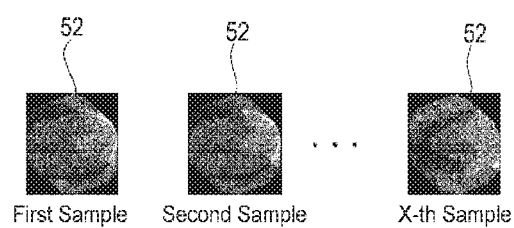
FIG. 15C is a view showing visualized data of the first to X-th samples.

As shown in FIGS. 15A and 15B, the third producing section 16 continuously paints the grids 23 with colors which are determined for respective samples in the grids 23. When colors for the first to X-th samples are continuously painted in each of the grids 23, continuous visualized data 52 such as shown in FIG. 15C are produced.

Figure 16:
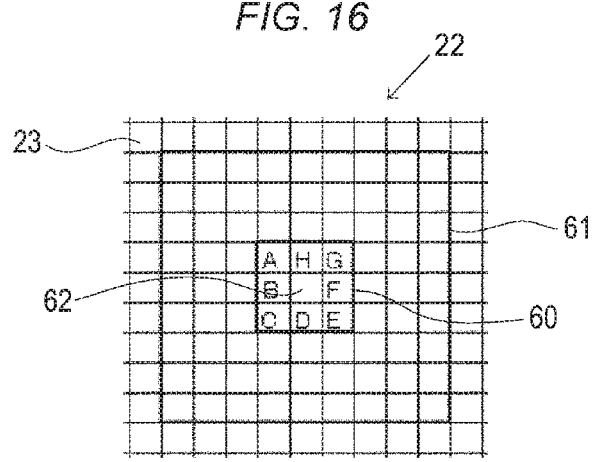
FIG. 16 is a view illustrating a method of detecting a phase singularity.
Figure 17:
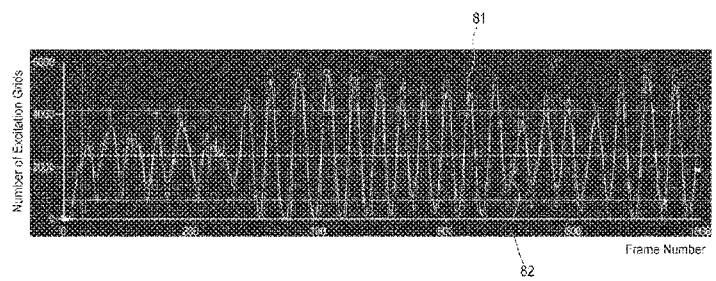
FIG. 17 is a view showing the number of excitation grids contained in frames constituting visualized data.
Figure 18:
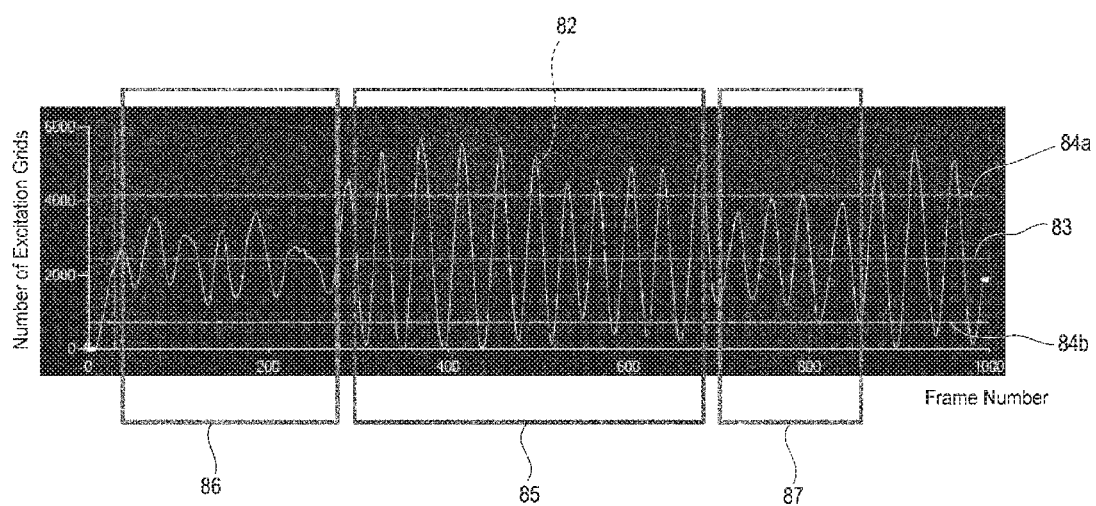
FIG. 18 is a view for determining the type of excitation dynamics of the myocardium.
Figure 19:
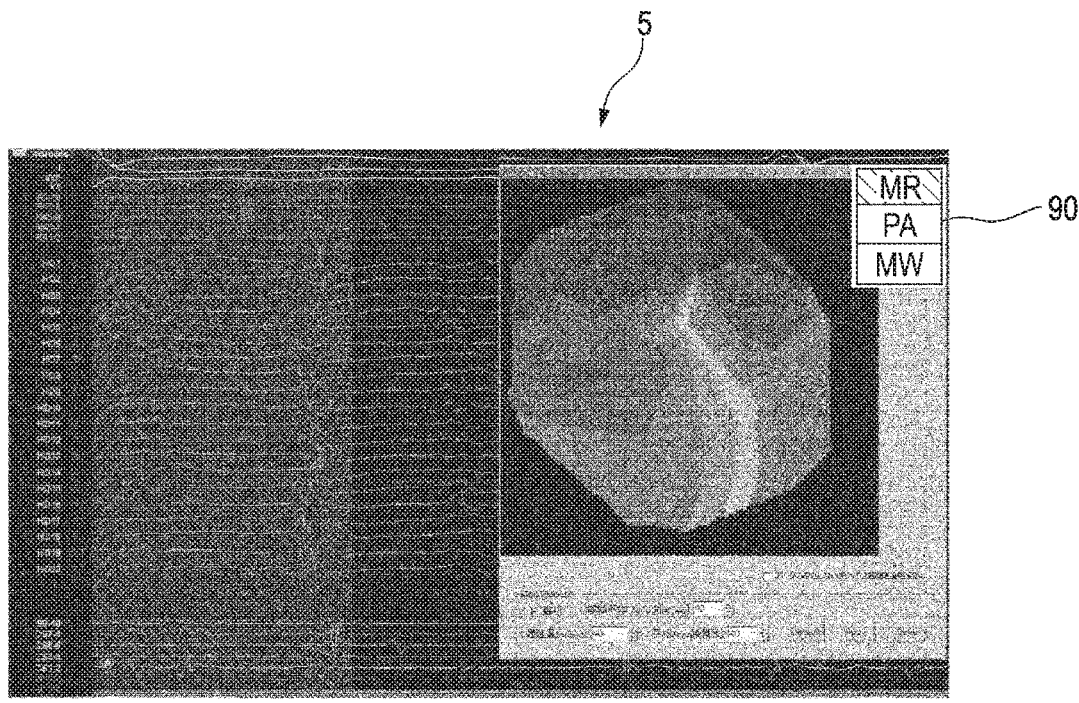
FIG. 19 illustrates an example of visualized data and type of excitation dynamics which are displayed on a monitor screen.

As shown in FIG. 16, then, the detecting section 17 extracts a first grid set 60 which is configured by a predetermined number (in the embodiment, 3×3) of grids 23, from the frame 22. The detecting section 17 further extracts a second grid set 61 that is configured by grids 23 which are centered on the first grid set 60, and the number (in the embodiment, 9×9) of which is larger than that in the first grid set 60. The detecting section 17 calculates whether the total of color differences between adjacent grids (from grid A to grid H) in the first grid set 60 is equal to or larger than a predetermined value or not. Specifically, (color difference between A and B)+(color difference between B and C)+ . . . +(color difference between H and A) is calculated. The detecting section 17 further calculates whether all of the 16 colors are contained in the second grid set 61 or not. When both the conditions are satisfied, the detecting section 17 detects the center of the first grid set 60 as a phase singularity 62 which is the center of swirl of the state of excitation in the myocardium.

In the determining section 4, then, the numbers of excitation grids contained in the frames in the visualized data produced by the third producing section 16 are sequentially calculated by the calculating section 18. Excitation grids mean grids indicating the state of excitation in the myocardium, and are grids which are painted with warm colors at R=255 (see the range 80 in FIG. 14A). For example, the numbers of excitation grids in the frames which are calculated by the calculating section 18 are shown as a graph 81 in FIG. 17. In the determining section 4, moreover, the moving averages of the numbers of excitation grids contained in frames (for example, 15 frames) in a predetermined time period are sequentially calculated by the calculating section 18. For example, the moving-averaged numbers of excitation grids are shown as a graph 82 in FIGS. 17 and 18.

The determining section 4 calculates the average value of the numbers of excitation grids, and determines plus and minus thresholds with reference to the calculated average number of excitation grids. For example, the average number of excitation grids is indicated as an average value of 83 in FIG. 18, and the plus and minus thresholds are shown as thresholds 84a, 84b in FIG. 18, respectively. The determining section 4 determines whether the moving-averaged numbers of excitation grids exceed the thresholds 84a, 84b or not. If the moving-averaged numbers of excitation grids exceed the thresholds, it is determined that the state of excitation dynamics of the myocardium is the PA. In the graph 82 shown in FIG. 18, the moving-averaged numbers of excitation grids exceed the thresholds 84a, 84b in, for example, a range 85, and it is determined that, in the time zone, the state of excitation dynamics of the myocardium is the PA. In the case where the moving-averaged numbers of excitation grids exceed the thresholds, furthermore, the positions of excitation grids in the frames may be specified, thereby determining whether the excitation wave occurs in the region of the cardiac catheter A or outside the region. This causes the state PA of excitation in the myocardium is further divided into two states.

If the moving-averaged numbers of excitation grids do not exceed the thresholds 84a, 84b (for example, in the case of the range 86 or 87 in FIG. 18), the determining section 4 determines the type of excitation dynamics of the myocardium based on the number of the phase singularities 62 of the frames detected by the detecting section 17. In the case where there are a plurality of total numbers of the phase singularities of the frames, the determining section 4 determines that the state of excitation dynamics of the myocardium is in the MW, and, in the case where there are not a plurality of total numbers, determines that the excitation dynamics of the myocardium is in the MR.

On the displaying section 5, the visualized data are continuously displayed in a time sequential manner to be shown as a moving image, whereby the manner of change in the state of excitation in the myocardium of the subject is displayed in real time. On the displaying section 5, in accordance with the change in the state of excitation in the myocardium, moreover, results of determinations of excitation dynamics of the myocardium are sequentially displayed in a type display region 90 in a display manner in which, for example, colors or characters indicating the types are used. In the type display region 90 in FIG. 19, it is displayed that the determination was the MR. Alternatively, the percentages of the types of excitation dynamics may be displayed in such a manner that, for example, Meandering Rotor=100%, Passive Activation=0%, Multiple Wavelets=0%.

In the case where waveforms having beat information which is sufficient for analysis are not obtained from one of the electrodes B of the cardiac catheter A, the grid 23 related to the electrode B may be omitted from the drawing of the visualized data in order to maintain the accuracy of the visualized data. In this case, it may be determined whether beat information is sufficient or not, based on the cycle length value.

In a conventional case where the medical person is to determine the type of excitation dynamics of the myocardium, visualized data indicating the state of excitation in the myocardium are produced, and the type of excitation dynamics is determined based on the visualized data. However, the myocardium during atrial fibrillation sometimes vibrates, for example, about 300 times per minute. It is difficult to visually correctly determine excitation dynamics from data of the myocardium which change at such a high speed. Conventionally, when the state of excitation in the myocardium is to be observed, therefore, the changing speed of measured visualized data is sometimes reduced to, for example, $1/10$. Moreover, visualized data which can be acquired from one cardiac catheter are limited to data of a part of the atrium, and therefore data which are sufficient for visual determination cannot be obtained in one measurement. In order to enhance the determination accuracy, therefore, it is necessary to acquire data from a plurality of locations in the atrium. In the conventional method, consequently, a long period of time is required to determine the type of excitation dynamics of the myocardium.

In the myocardial excitation determining apparatus 1 of the embodiment, by contrast, the type of excitation dynamics of the myocardium during atrial fibrillation is automatically determined based on the total number of excitation grids contained in the visualized data. Moreover, the type of excitation dynamics of the myocardium during atrial fibrillation is automatically determined based on the total number of phase singularities. When a result of the automatic determination is referred, therefore, the medical person can determine the type of excitation dynamics of the myocardium, more correctly and in a shorter time period as compared with the case where the determination is visually performed as in the prior art. Moreover, the determination is performed based on a plurality of parameters (the total numbers of excitation grids and phase singularities), and therefore the meandering rotor, passive activation, and multiple wavelets which are typical types of excitation dynamics can be automatically determined from one another.

Together with the moving image illustrating a change of the state of excitation in the myocardium, a result (type) of the automatic determination is displayed on the displaying section 5 so as to be corresponded to the change of the state of excitation. Therefore, the medical person can easily know the type itself of excitation dynamics of the myocardium, and the manner of the type change. In the case where the percentages of the types of excitation dynamics are displayed, it is sometimes not necessary to check the moving image to the end.

According to the configuration, therefore, it is possible to provide a myocardial excitation determining apparatus which can support the determination of excitation dynamics of the myocardium during atrial fibrillation.

Embodiment 2

Next, Embodiment 2 will be described. Hereinafter, components which are identical with those of Embodiment 1 are denoted by the same reference numerals, and their description will be omitted.

Figure 20:
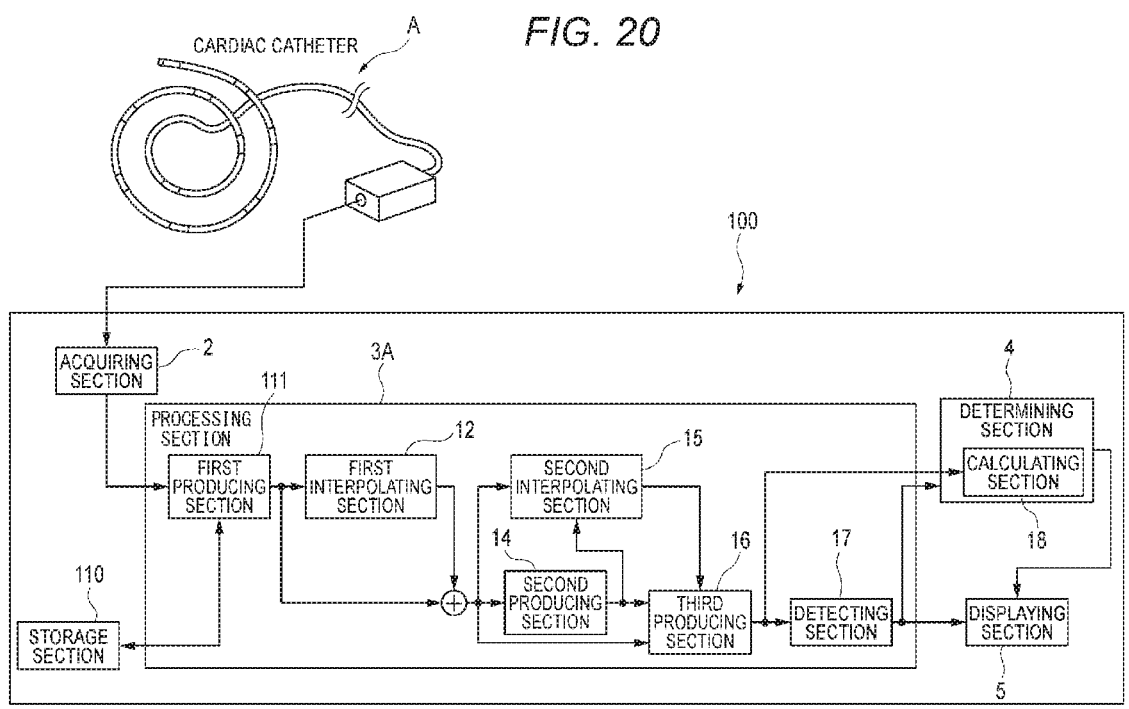
FIG. 20 is a diagram of a myocardial excitation determining apparatus of Embodiment 2 of the invention.

As shown in FIG. 20, a myocardial excitation determining apparatus 100 of Embodiment 2 includes the acquiring section 2, a processing section 3A, a storage section 110, the determining section 4, and the displaying section 5. The processing section 3 includes a first producing section 111, the first interpolating section 12, the second producing section 14, the second interpolating section 15, the third producing section 16, and the detecting section 17.

Figure 21:
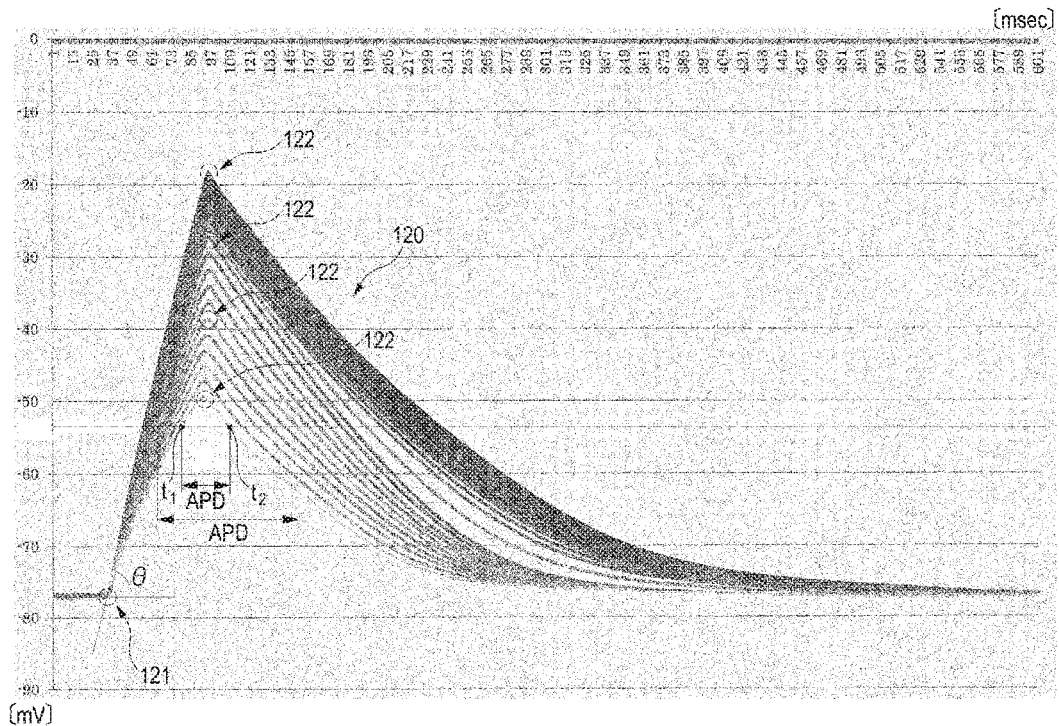
FIG. 21 illustrates an action potential unit waveform for producing the action potential waveform.

The storage section 110 stores a plurality of action potential unit waveforms 120 which are as shown in FIG. 21, and which are previously produced. The action potential unit waveforms 120 are obtained by applying a temporal moving averaging process on an action potential waveform in human atrial muscle under structural remodeling which is derived by computer simulation. The term "structural remodeling" means a histoanatomical change which appears in a pathological condition of the atrial muscle. In each of the action potential unit waveforms 120, the rising from the start point 121 to the peak 122 is gentler (the rising angle q is smaller)

as compared with that in an ideal model of a unit waveform contained in the action potential waveforms in the myocardium. The storage section 110 is connected to the first producing section 111.

The first producing section 111 produces pseudo action potential waveforms by using the action potential unit waveforms 120 with respect to the plurality of intracardiac electrocardiograms which are acquired by the acquiring section 2. In the following description of Embodiment 2, a pseudo action potential waveform 25 is also referred to simply as an action potential waveform 25.

With respect to each of the action potential waveforms output from the first producing section 111 and the first interpolating section 12, the second producing section 14 produces a shifted waveform which is shifted in time phase by a predetermined time from the action potential waveform.

The third producing section 16 produces a phase portrait based on the action potential waveforms output from the first producing section 111 and the first interpolating section 12, the shifted waveforms output from the second producing section 14, and the action potential waveforms and shifted waveforms output from the second interpolating section 15. Moreover, the third producing section 16 calculates the phase based on the phase portrait, and produces visualized data (Phase Map) indicating the state of excitation in the myocardium.

The acquiring section 2, the first interpolating section 12, the second interpolating section 15, the detecting section 17, the determining section 4, and the displaying section 5 are configured in a same or a similar manner as the respective sections in Embodiment 1.

Next, the operation of the myocardial excitation determining apparatus 100 will be described.

The operation which is performed until the intracardiac electrocardiogram waveforms 21a to 21j recorded by the cardiac catheter A are placed on the grids 23 is similar to that which is performed before and including the description of FIG. 4B in Embodiment 1.

With respect to the recorded intracardiac electrocardiogram waveforms 21a to 21j, thereafter, the first producing section 11 produces the action potential waveforms 25 by using the action potential unit waveforms 120.

Figure 22:
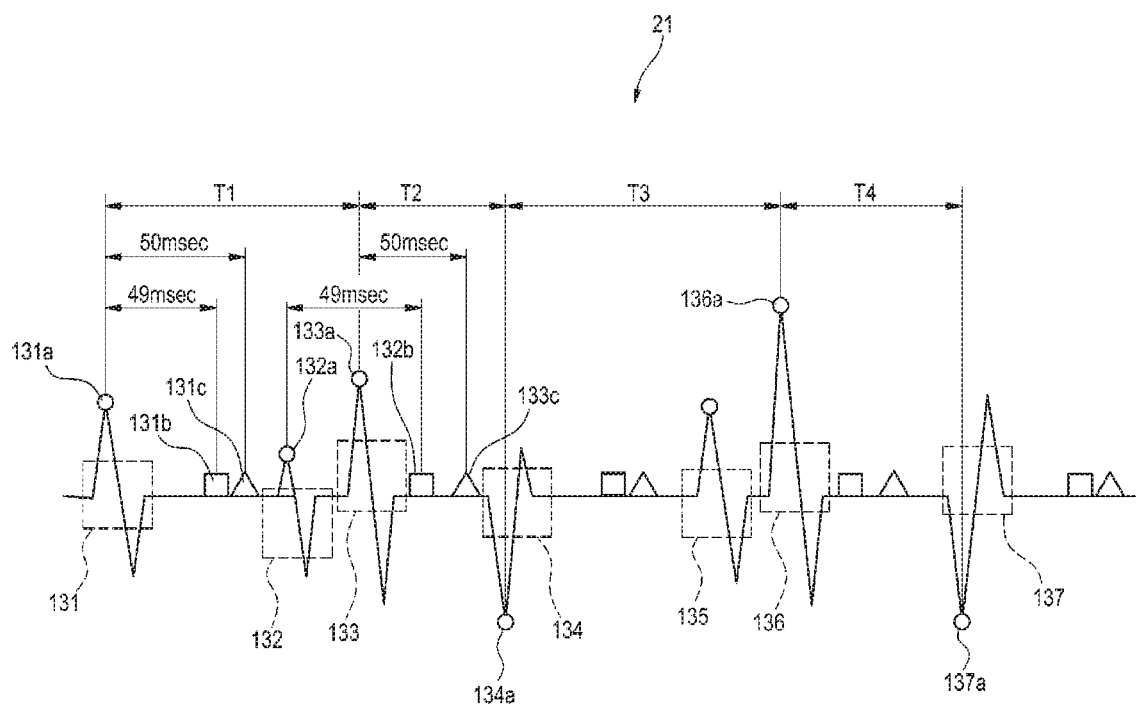
FIG. 22 illustrates a procedure of detecting the waveform of myocardial excitation from an intracardiac electrocardiogram waveform.

In order to produce the action potential waveforms 25, as shown in FIG. 22, for example, the first producing section 11 first detects beats satisfying predetermined conditions, as candidate waveforms of myocardial excitation, from the recorded intracardiac electrocardiogram waveforms 21. Specifically, beats which satisfy conditions that the lateral width w is 10 msec. or shorter, and the vertical width h is 0.1 mV or higher are detected (with respect to the lateral width w and the vertical width h, see FIG. 6C). In the case of the intracardiac electrocardiogram waveform 21 shown in FIG. 22, as beats satisfying the conditions, seven beats contained in the broken-line rectangles 131 to 137 are detected as candidate waveforms of myocardial excitation.

The first producing section 11 further detects beats satisfying predetermined conditions as the waveform of myocardial excitation, from the detected candidate waveforms of myocardial excitation. With reference to the candidate waveforms of myocardial excitation, specifically, the first producing section 11 sets a search time period when another candidate waveform of myocardial excitation is searched, and a search exclusion time period when another candidate waveform of myocardial excitation is not searched. In this case, the search time period (for example, 49 msec.) is set to a time period which is shorter than the search exclusion time period (for example, 50 msec.).

As shown in FIG. 22, the first producing section 11 detects, in the intracardiac electrocardiogram waveform 21, detects a beat which is first contained in the broken-line rectangle 131, as a candidate waveform of myocardial excitation. The first producing section 11 searches whether or not another candidate waveform of myocardial excitation (a waveform contained in the broken-line rectangle) exists between the peak (the circle symbol 131a) of the detected candidate waveform of myocardial excitation, and the square symbol 131b after elapse of the search time period (49 msec.). In the embodiment, another candidate waveform of myocardial excitation does not exist in the search time period. In the embodiment, therefore, the beat contained in the broken-line rectangle 131 is detected as the initial waveform of myocardial excitation. The first producing section 11 sets the time period between the peak (the circle symbol 131a) of the detected waveform of myocardial excitation, and the triangle symbol 131c after elapse of 50 msec., as a detection exclusion time period when another candidate waveform of myocardial excitation is not detected.

After the detection exclusion time period (after and including the triangle symbol 131c), the first producing section 11 detects a beat contained in a broken-line rectangle 132 as the next candidate waveform of myocardial excitation. Similarly with the above-described search, the first producing section 11 searches whether or not another candidate waveform of myocardial excitation exists between the peak (the circle symbol 132a) of the detected candidate waveform of myocardial excitation, and the square symbol 132b after elapse of the search time period. In the case of the embodiment, a beat contained in a broken-line rectangle 133 is detected as another candidate waveform of myocardial excitation. The first producing section 11 compares the amplitudes (P-P values) of the two detected candidate waveforms of myocardial excitation (the beats contained in the broken-line rectangles 132, 133) with each other, and detects the candidate waveform having the larger amplitude, as the waveform of myocardial excitation. In the embodiment, the beat contained in the broken-line rectangle 133 is detected as the waveform of myocardial excitation. The first producing section 11 sets the time period between the peak (the circle symbol 133a) of the detected candidate waveform of myocardial excitation, and the triangle symbol 133c after elapse of 50 msec., as the detection exclusion time period in a manner similar to the above. The beat in the broken-line rectangle 132 which is not detected as the waveform of myocardial excitation is eliminated from waveforms for producing the action potential waveform 25.

When the above-described detecting process is repeated, in the intracardiac electrocardiogram waveforms 21 shown in FIG. 22, beats contained in the broken-line rectangles 131, 133, 134, 136, 137 are detected as waveforms of myocardial excitation.

Then, the first producing section 11 detects the time intervals between the detected waveforms (between the unit waveforms) of myocardial excitation. Specifically, the time interval T1 between the peak (the circle symbol 131a) of the beat contained in the broken-line rectangle 131, and the peak (the circle symbol 133a) of the beat contained in the broken-line rectangle 133 is detected. Same or similarly, the time interval T2 between the circle symbol 133a and the circle symbol 134a, the time interval T3 between the circle symbol 134a and the circle symbol 136a, and the time interval T4 between the circle symbol 136a and the circle symbol 137a are detected.

When the action potential waveforms 25 are to be produced by using the action potential unit waveforms 120, calculations are performed under the assumption that the detected time intervals T1 to T4 between the waveforms of myocardial excitation correspond to unit waveforms (hereinafter, referred to as unit action potential waveforms) CL1 to CL4A contained in the action potential waveforms 25 to be produced, respectively.

Figure 23:
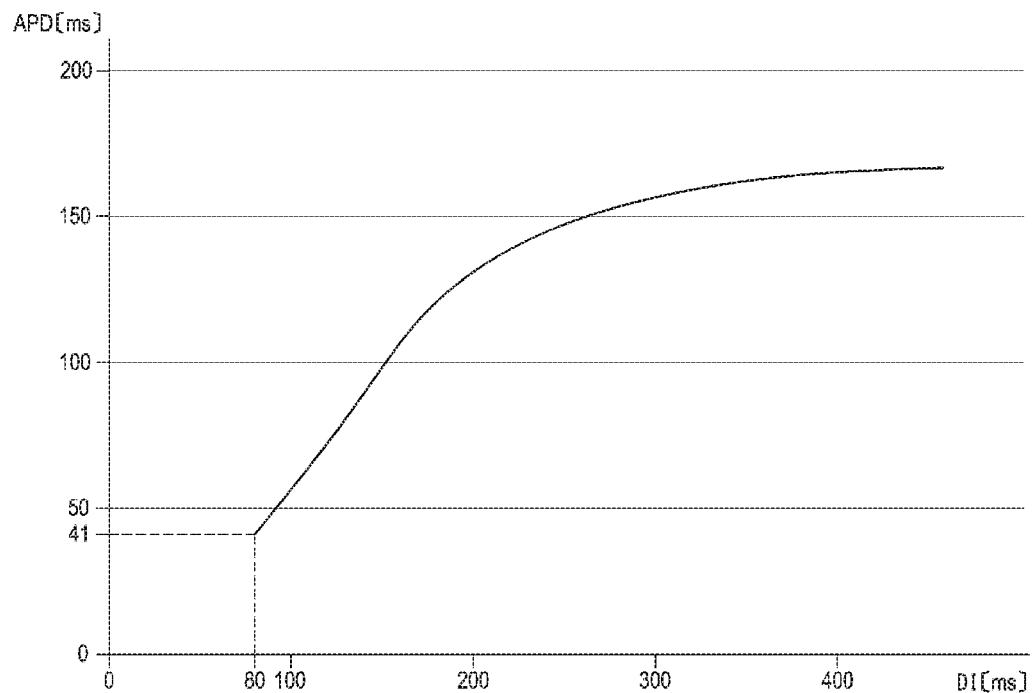
FIG. 23 is a graph illustrating relationships between a diastolic interval and action potential duration of an action potential unit waveform.

The first producing section 11 applies the shortest APD (41 msec.) shown in the graph of FIG. 23, to the APD value of the unit action potential waveform which is produced with respect to the initial waveform of myocardial excitation (the beat contained in the broken-line rectangle 131). The first producing section 11 subtracts the shortest APD from the CL1 (T1) to obtain the value of the DI1 (DI1=CL1−shortest APD), and obtains the value of the APD with respect to the obtained value of the DI1 from the graph of FIG. 23. The obtained value of the APD is the value of the APD2 of the unit action potential waveform which is produced with respect to the second waveform of myocardial excitation (the beat contained in the broken-line rectangle 133).

Same or similarly, the values of the APDs (APD3, APD4, etc.) of unit action potential waveforms which are produced with respect to the third and subsequent waveforms of myocardial excitation are obtained.

Based on the obtained values of the APDs, then, the first producing section 11 selects action potential unit waveforms which are to be used in the production of the action potential waveforms 25, from the action potential unit waveforms 120 shown in FIG. 21. In each of the action potential unit waveforms 120 of FIG. 21, specifically, the time interval between two points (for example, between $t_1$ and $t_2$) indicating −53 mV is set as the value of the APD of the action potential unit waveform 120. Then, action potential unit waveforms 120 having the value of the APD which is close to the thus obtained values of the APDs (APD1, APD2, etc.) are sequentially selected.

Figure 24:
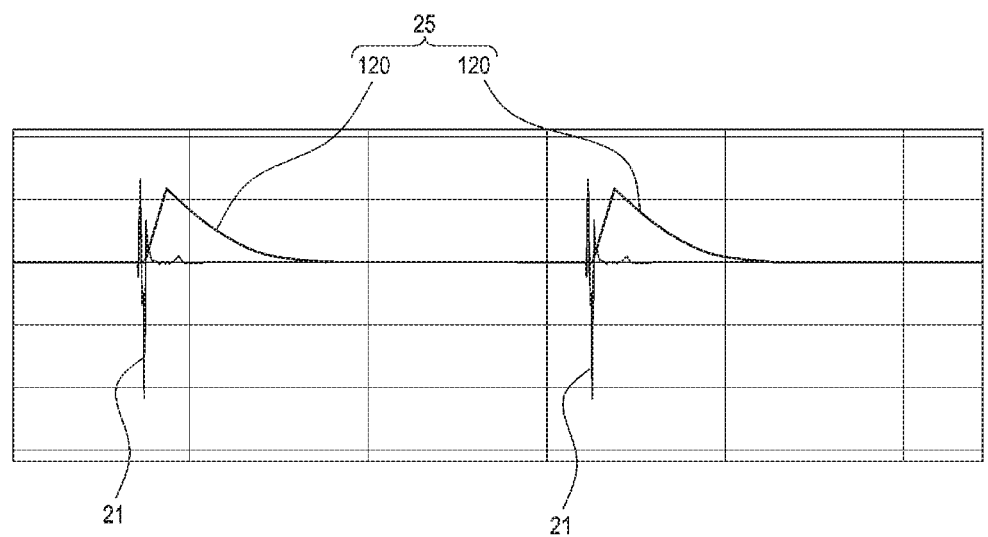
FIG. 24 illustrates an intracardiac electrocardiogram waveform to which an action potential unit waveform is applied.

The selected action potential unit waveforms 120 are displayed as waveforms for producing the action potential waveforms 25, corresponding to the intracardiac electrocardiogram waveform 21 as shown in FIG. 24. The display position of each of the action potential unit waveforms 120 relative to the intracardiac electrocardiogram waveform 21 is as shown in FIG. 25. When the intracardiac electrocardiogram waveform 21 is full-wave rectified to produce the full-wave rectified waveform 24, and a moving averaging process is applied to the full-wave rectified waveform 24 to produce the action potential waveform 25, for example, the time phase of the peak 25P of the action potential waveform 25 is the position of the start point 121 of the action potential unit waveform 120.

Same or similarly, the first producing section 11 produces the action potential waveforms 25a to 25j with respect to the intracardiac electrocardiogram waveforms 21a to 21j.

In a same or a similar manner as Embodiment 1, then, the first interpolating section 12 sets the positions of virtual electrodes, and interpolates the action potential waveform 25k and the like with respect to the set virtual electrodes.

In Embodiment 2, the action potential unit waveforms are used, and therefore the correction in which, as in Embodiment 1, the amplitudes of the action potential waveforms are justified by the correcting section is not performed.

Then, the second producing section 14 calculates the mean APD of the values of the APDs (APD3, APD4, etc.) of the unit action potential waveforms, and, similarly with Embodiment 1, produces the shifted waveforms 40a to 40k. The action potential waveforms 25a to 25k and the shifted waveforms 40a to 40k are placed on the grids 23 where the electrodes and the virtual electrodes are disposed, respectively (see FIG. 11B).

The processing operations which are performed in the following steps in the second interpolating section 15, the third producing section 16, the detecting section 17, and the determining section 4 (including the calculating section 18) and the displaying section 5 are similar to those in the description of Embodiment 1.

Also the thus configured myocardial excitation determining apparatus 100 attains effects similar to those in Embodiment 1.

The invention is not limited to the above-described embodiments, and may be adequately subjected to modification, improvement, and the like. In addition, the materials, shapes, dimensions, numerical values, forms, numbers, placement places, and the like of the components of the above-described embodiments are arbitrary and not limited insofar as the invention is achieved.

In the embodiments, for example, phase portraits and visualized data are produced by using action potential waveforms and shifted waveforms, and the type of excitation dynamics of the myocardium is determined based on the visualized data. However, the invention is not limited to the configuration. For example, the Hilbert conversion may be performed on intracardiac electrocardiograms to produce phase portraits and visualized data, and the type of excitation dynamics of the myocardium may be determined based on the visualized data.

The present application is based on Japanese Patent Application No. 2016-050782, filed on Mar. 15, 2016, the entire contents of which are incorporated herein by reference.

The invention claimed is:

1. A myocardial excitation determining apparatus comprising:
    an acquiring section configured to acquire an intracardiac electrocardiogram of a subject;
    a processor configured to produce visualized data indicating a state of excitation in a myocardium, based on the intracardiac electrocardiogram and determine a type of excitation dynamics of the myocardium based on the visualized data,
    wherein the processor is configured to:
        produce the visualized data from a plurality of frames per predetermined time unit,
        partition each of the frames into a plurality of grids,
        calculate total numbers of excitation grids for each frame of the plurality of frames indicating the state of excitation in the myocardium, from among the plurality of grids constituting the frames, and
        determine the type of the excitation dynamics of the myocardium, based on the total numbers of excitation grids for each frame of the plurality of frames.

2. The apparatus according to claim 1, wherein the processor comprises a detecting section configured to detect a phase singularity indicating a center of swirl of the state of excitation in the myocardium, for each frame of the plurality of frames based on the visualized data, and
    wherein the processor is configured to determine the type of the excitation dynamics of the myocardium, for each frame of the plurality of frames based on the total numbers of excitation grids and a total number of phase singularities of the plurality of frames.

3. The apparatus according to claim 1, further comprising a displaying section configured to display the type of excitation dynamics.

4. The apparatus according to claim 2, further comprising a displaying section configured to display the type of excitation dynamics.

5. A method of a myocardial excitation determining apparatus determining a type of excitation in a myocardium, the method comprising:
- acquiring an intracardiac electrocardiogram of a subject;
- producing visualized data indicating a state of excitation in the myocardium, based on the intracardiac electrocardiogram from a plurality of frames per predetermined time unit, wherein each frame of the plurality of frames is partitioned into a plurality of grids,
- calculating total numbers of excitation grids for each frame of the plurality of frames indicating the state of excitation in the myocardium, from among the plurality of grids constituting the frames;
- determining a type of excitation dynamics of the myocardium based on the total numbers of excitation grids for each frame of the plurality of frames.

* * * * *